(12) United States Patent
Blair et al.

(10) Patent No.: US 9,012,207 B2
(45) Date of Patent: Apr. 21, 2015

(54) BIOSENSORS INCLUDING METALLIC NANOCAVITIES

(75) Inventors: Steven M. Blair, Salt Lake City, UT (US); Farhad Mahdavi, Salt Lake City, UT (US); Yongdong Liu, Salt Lake City, UT (US); James N. Herron, Salt Lake City, UT (US); Ajay Nahata, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 594 days.

(21) Appl. No.: 11/497,581

(22) Filed: Aug. 2, 2006

(65) Prior Publication Data
US 2010/0256016 A1    Oct. 7, 2010

Related U.S. Application Data

(60) Provisional application No. 60/795,110, filed on Apr. 26, 2006, provisional application No. 60/705,216, filed on Aug. 2, 2005.

(51) Int. Cl.
| | |
|---|---|
| *C12M 1/34* | (2006.01) |
| *G01N 33/543* | (2006.01) |
| *B82Y 15/00* | (2011.01) |
| *B82Y 20/00* | (2011.01) |
| *B82Y 30/00* | (2011.01) |
| *G01N 21/64* | (2006.01) |

(Continued)

(52) U.S. Cl.
CPC .......... *G01N 33/54373* (2013.01); *B82Y 15/00* (2013.01); *B82Y 20/00* (2013.01); *B82Y 30/00* (2013.01); *G01N 21/648* (2013.01); *G01N 21/7746* (2013.01); *G02B 5/008* (2013.01); *G02B 2207/101* (2013.01)

(58) Field of Classification Search
None
See application file for complete search history.

(56) References Cited

U.S. PATENT DOCUMENTS

| | | | |
|---|---|---|---|
| 5,033,291 A | 7/1991 | Podoloff et al. | |
| 5,338,430 A * | 8/1994 | Parsonage et al. | ............ 204/412 |

(Continued)

FOREIGN PATENT DOCUMENTS

WO       WO 03005890 A2 *    1/2003

OTHER PUBLICATIONS

Schechter, "Bright new World," New Scientist, vol. 178, p. 31-33 (2003).

(Continued)

*Primary Examiner* — Chris L Chin
(74) *Attorney, Agent, or Firm* — Thorpe North & Western, LLP

(57) ABSTRACT

A biomolecular assay includes a substrate with a metallic layer on at least one surface thereof. The metallic film includes nanocavities. The nanocavities are configured to enhance signals that are representative of the presence or amount of one or more analytes in a sample or sample solution, and may be configured to enhance the signal by a factor of about two or more or by a factor of about three or more. Such signal enhancement may be achieved with nanocavities that are organized in an array, randomly positioned nanocavities, or nanocavities that are surrounded by increased surface area features, such as corrugation or patterning, or nanocavities that have quadrilateral or triangular shapes with tailored edge lengths, or with a plurality of nanoparticles. Methods for fabricating biomolecular substrates and assay techniques in which such biomolecular substrates are used are also disclosed.

27 Claims, 10 Drawing Sheets

(51) Int. Cl.
G01N 21/77 (2006.01)
G02B 5/00 (2006.01)

(56) References Cited

U.S. PATENT DOCUMENTS

| | | | |
|---|---|---|---|
| 5,408,873 | A | 4/1995 | Schmidt et al. |
| 5,677,196 | A * | 10/1997 | Herron et al. ............... 436/518 |
| 5,678,448 | A | 10/1997 | Fullen et al. |
| 5,770,456 | A | 6/1998 | Holmes |
| 5,929,332 | A | 7/1999 | Brown |
| 6,225,061 | B1 * | 5/2001 | Becker et al. ................. 506/16 |
| 6,514,768 | B1 * | 2/2003 | Guire et al. ................. 436/518 |
| 6,579,680 | B2 | 6/2003 | Frutos et al. |
| 6,777,244 | B2 | 8/2004 | Pepper et al. |
| 7,171,331 | B2 | 1/2007 | Vock et al. |
| 7,332,344 | B2 | 2/2008 | Morgan |
| 7,648,441 | B2 | 1/2010 | Silk |
| 2001/0041339 | A1 * | 11/2001 | Anderson et al. ................ 435/6 |
| 2002/0009394 | A1 * | 1/2002 | Koster et al. .................. 422/65 |
| 2002/0081714 | A1 * | 6/2002 | Jain et al. .................. 435/287.2 |
| 2003/0017450 | A1 * | 1/2003 | Oon et al. ........................ 435/5 |
| 2003/0032076 | A1 * | 2/2003 | Duffy et al. ................ 435/7.92 |
| 2003/0068446 | A1 * | 4/2003 | Mirkin et al. ............. 427/430.1 |
| 2003/0087292 | A1 | 5/2003 | Chen et al. |
| 2003/0148401 | A1 | 8/2003 | Agrawal et al. |
| 2003/0173501 | A1 | 9/2003 | Thio et al. |
| 2003/0178641 | A1 | 9/2003 | Blair et al. |
| 2003/0180191 | A1 * | 9/2003 | Suzuki et al. ................. 422/102 |
| 2003/0222232 | A1 * | 12/2003 | Welland et al. ............... 250/573 |
| 2004/0009530 | A1 * | 1/2004 | Wilson et al. ................. 435/7.1 |
| 2004/0029152 | A1 * | 2/2004 | Ishida .............................. 435/6 |
| 2004/0125190 | A1 * | 7/2004 | Koyama ........................ 347/105 |
| 2004/0180379 | A1 * | 9/2004 | Van Duyne et al. .......... 435/7.1 |
| 2004/0224321 | A1 | 11/2004 | Nicolau et al. |
| 2006/0099704 | A1 * | 5/2006 | Predki et al. ............... 435/287.2 |
| 2007/0202478 | A1 | 8/2007 | Al-Obaidi et al. |
| 2008/0039339 | A1 | 2/2008 | Hassibi et al. |
| 2010/0256016 | A1 | 10/2010 | Blair et al. |

OTHER PUBLICATIONS

Liedberg et al., "Surface Plasmon resonance for gas detection and biosensing," Sen. Actuators, vol. 4, p. 299-304 (1983).
Bianchi et al., "Biosensor technology and surface Plasmon resonance for real-time detection of HIV-1 genomic sequences amplified by polymerase chain reaction," Clin. Diagnostic Virology, vol. 8, p. 199-208 (1997).
Yguerabide et al., "Light-scattering submicroscopic particles as highly fluorescent analogs and their use as tracer labels in clinical and biological applications," Anal. Biochem., vol. 262, No. 2, (Sep. 1998), p. 137-156.
Taton et al., "Scanometric DNA array detection with nanoparticle probes," Science, vol. 289, p. 1757-1760 (2000).
Hirsch et al., "A whole blood immunoassay using gold nanoshells," Anal. Chem., vol. 75, (2003), 2377-2381.
Wokaun et al., "Energy transfer in surface enhanced luminescence," J. Chem. Phys., vol. 79, No. 1, p. 509-514 (1983).
Malicka et al., "Effects on fluorophore-to-silver distance on the emission of cyanine-dye-labeled obligonucleotides," Anal. Biochem., vol. 315, p. 57-66 (2003).
Kneipp et al., "Extremely large enhancement factors in surface-enhanced Raman scattering for molecules on colloidal gold clusters," Appl. Spectros., vol. 52, p. 1493-1497 (1998).
Shalaev et al., "Optical properties of self-affine thin films," Phys. Rev. B, vol. 54, p. 8235-8242 (1996).
Ditlbacher et al., "Electromagnetic interaction of fluorophores with designed 2D silver nanoparticle arrays," Appl. Phys. B, vol. 73, (2001), p. 373-377.
Felidj et al., "Optimized surface-enhanced Raman scattering on gold nanoparticle arrays." Appl. Phys. Lett., vol. 82, No. 18, p. 3095-3097 (2003).

Ebbeson et al., "Extraordinary optical transmission through sub-wavelength hole arrays," Nature, vol. 391, p. 667-669 (1998).
Lezec et al., "Diffracted evanescent wave model for enhanced and suppressed optical transmission through subwavelength hole arrays," Optics Express, vol. 12, No. 16, p. 3629-3651 (2004).
Avrutsky et al., "Surface-plasmon-assisted resonant tunneling of light through a periodically corrugated thin metal film," Opt. Lett., vol. 25, p. 595-597 (2000).
Sarychev et al., "Resonance transmittance through a metal film with subwavelength holes," IEEE J. Quantum Electron, vol. 38, p. 956-963 (2002).
Martin-Moreno et al., "optical transmission through subwavelength hole arrays," Opt. Express, vol. 12, p. 3619-3628 (May 2004).
Liu et al., "Fluorescence enhancement from an array of subwavelength metal apertures," Opt. Lett., vol. 28, p. 507-509 (2003).
Liu et al., "Biosensing based upon molecular confinement in metallic nanocavity arrays," nanotechnology, vol. 15, p. 1368-1374 (2004).
Liu et al., "Fluorescence transmission through 1-D and 2-D periodic metal films," Opt. Express, vol. 12, No. 16, p. 3686-3693 (2004).
Rigneault et al., "Enhancement of single-molecule fluorescence detection in subwavelength apertures," Physical Review Letters 95, p. 117401 (2005).
Wenger et al., "Single-molecule fluorescence in rectangular nano-apertures," Optics Express, vol. 13, p. 7035-7044 (2005).
Liu et al., "Enhanced fluorescence transduction properties of metallic nanocavity arrays," IEEE Journal of Selected Topics in Quantum Electronics, vol. 11, p. 778-784 (2005).
Maron et al., "Impact of laboratory molecular diagnosis on contemporary diagnostic criteria for genetically transmitted cardiovascular diseases: hypertropic cardiomyopathy, long-QT syndrome, and Marfan syndrome," Circulation, vol. 98, p. 1460-1471 (1998).
Hacia, "Resequencing and mutational analysis using obligonucleotide microarrays," Nature Genetics, vol. 21, p. 42-47 (1999).
Moerner et al., "Methods of single-molecule fluorescence spectroscopy and microscopy," Review of Scientific Instruments, vol. 74, p. 3597-3619 (2003).
Belosludtsev et al., "Organism identification using a genome sequence independent universal microarray probe set," Biotechniques, vol. 37, p. 654-660 (2004).
Saluz et al., "Fundamentals of DNA-chip/array technology for comparative gene-expression analysis," Current Science, vol. 83, p. 829-833 (2002).
Chou et al., "Nanoimprint lithography," Journal of Vacuum Science and Technology B, vol. 14, p. 4129-4133 (1996).
Prime et al., "Adsorption of proteins onto surfaces containing end-attached oligo(ethylene oxide): a model system using self-assembled monolayers," Journal the American Chemical Society, vol. 115, p. 10714-10721 (1993).
Disley et al., "Covalent coupling of immunoglobulin G to self assembled monolayers as a method for immobilizing the interfacial-recognition layer of a surface Plasmon resonance immunosensor," Biosensors and Bioelectronics, vol. 13, p. 1213-1225 (1998).
Smolyaninov et al., "Near-field optical microscopy of two-dimensional photonic and plasmonics crystals," Physical Review B, vol. 59, p. 2454-2460 (1999).
Ermuschev et al., "Surface enhancement of local optical fields and the lightning-rod effect," Quantum Electronics, vol. 23, p. 435-440 (1993).
Gruhlke et al., "Surface-plasmon cross-coupling in molecular fluorescence near a corrugated thin metal film," physical Review letters, vol. 56, p. 2838-2841 (1986).
Gruhlke et al., "Optical emission from coupled surface plasmons," Optics letters, vol. 12, p. 364-366 (1987).
Herron et al., "Planar waveguide biosensors for nucleic acid hybridization reactions," Proceedings SPIE, vol. 3913, p. 177-184 (2000).
Myszka et al., "Extending the range of rate constants available from BIACORE: interpreting mass transport-influenced binding data," Biophysical Journal, vol. 75, p. 583-594 (1998).
Dai et al., "Use of hybridization kinetics for differentiating specific from non-specific binding to oligonucleotide microarrays," Nucleic Acids Research, vol. 30 (2002), e86.

(56) References Cited

OTHER PUBLICATIONS

Heaton et al., "Electrostatic surface Plasmon resonance: direct electric field-induced hybridization and denaturation in monolayer nucleic acid films and label-free discrimination of the base mismatches," Proceedings of the National Academy of Sciences, vol. 98, p. 3701-3704 (2001).
Su et al., "Kinetics of heterogeneous hybridization on indium tin oxide with and without an applied potential," Electrophoresis, vol. 23, p. 1551-1557 (2002).
Lee et al., "Nanoscale two-dimensional patterning on Si(001) by large-area interferometric lithography and anisotropic wet etching," Journal of Vacuum Science & Technology B, vol. 22, p. 1949-1952 (2004).
Murray et al., "Transition from localized surface Plasmon resonance to extended surface Plasmon-polariton as metallic nanoparticles merge to from a periodic hole array," Physical Review B, vol. 69, p. 165407 (2004).
Martin-Moreno et al., "Theory of extraordinary optical transmission through subwavelength hole arrays," Physical Review Letters, vol. 86, p. 1114-1117 (2001).
Thio et al., "Enhanced light transmission through a single subwavelength aperture," Optic Letter, vol. 26, p. 1972-1974 (2001).
Malicka et al., "DNA hybridization assays using metal-enhanced fluorescence," Biochemical and Biophysical Research Communications, vol. 306, p. 213-218 (2003).
Blanco et al., "Spontaneous light emission in complex nanostructures," Physical Review B, vol. 69, p. 205414 (2004).
Nahata et al., "Enhanced nonlinear optical conversion using periodically nanostructured metal films," Optics Letters, vol. 28, p. 423-425 (2003).
Fleischmann et al., "Raman spectra of pyridine adsorbed at a silver electrode," Chemical Physics Letters, vol. 26, p. 163-166 (1974).
Craighead et al., "Optical absorption of small metal particles with adsorbed dye coats", Optics Letters, vol. 6, 248-250 (1981).
Ditlbacher et al., "Electromagnetic intereaction of fluorophores with designed 2D silver nanoparticle arrays," Applied Physics B, vol. 73, (2001), p. 373-377.
Bruchez et al., "Semiconductor nanocrystals as fluorescent biological labels," Science, vol. 281, p. 2013-2016 (1998).
Chan et al., "Quantum dot bioconjugates for ultrasensitive nonisotropic detection," Science, vol. 281, p. 2016-2018 (1998).
Mahdavi et al., "Modeling Fluorescence Enhancement from Metallic Nanocavities", Plasmonics, vol. 2, p. 129-141 (2007).
Gerard et al., "Nanoaperture-enhanced fluorescence: Towards higher detection rates with plasmonic metals," Physical Review B, vol. 77, 045413 (2008).
PCT/US2006/030003, Blair et al., Aug. 2, 2006, International Search Report, Jul. 8, 2008.
PCT/US2006/030003, Blair et al., Aug. 2, 2006, Written Opinion, Oct. 18, 2006.
Liu Yongdong et al., "Biosensing based upon molecular confinement in metallic nanocavity arrays," Plasmonics in Biology and Medicine II, Proceedings of SPIE vol. 5703, Dec. 8, 2009, p. 99-106.
Liu et al., "Biosensing based upon molecular confinement in metallic nanaocavity arrays," IEEE, 2004 pp. 31-32.
Haes et al., "A nanoscale optical biosensor: sensitivity and selectivity of an approach based on the localized surface plasmon resonance spectroscopy of triangular silver nanoparticals," J. Am. Chem Soc 2002, 124, 10596-10604.
Chen, "Enhancement of the resolution of surface plasmon resonance biosensors by control of the size and distribution of nanoparticles," Optical Letters, Jun. 15, 2004, pp. 1390-1392, vol. 29, No. 12.
Liu et al., "The enhancement effect of gold nanoparticles as a surface modifier on DNA sensor sensitivity," Biochemcial and Biophysical Research Communications 311 (2004), pp. 3-7.
Song, "Ultrahigh-Q Nanocavity based on photonic-crystal double heterostructure," Quantum Electronics and Laser Science Conference, 2005, pp. 407-409.
Levene, "Zero-mode waveguides for single-molecule analysis at high concentrations," Science, Jan. 31, 2003, vol. 299, pp. 682-686.
Martin-Moreno et al., "Optical transmission through circular hole arrays in optically thick metal films,"Optics Express, Aug. 9, 2004, pp. 3619-3628, vol. 12, No. 16.
Blair et al., "Enhancement of molecular fluorescence by metallic nanocavities," Proc of SPIE vol. 5927, 2005, 5 pages.
Dodge et al.; A Microfluidic Platform Using Molecular Beacon-Based Temerature Calibration for Thermal Dehybridization of Surface-Bound DNA; Anal. Chem.; 2004; vol. 76; pp. 1778-1787.
Rajendran et al.; In Vitro Selection of Mosecular Beacons.
U.S. Appl. No. 11/633,980, filed Dec. 4, 2006; Alexander M. Chagovetz; office action issued Apr. 28, 2011.
U.S. Appl. No. 12/042,516, filed Mar. 5, 2008; Steven M. Blair; office action issued Apr. 29, 2011.
Bishop et al.; A Competitive Kinetic Model of Nucleic Acid Hybridization in the Presence of Point Mutants; Biophysical Journal; Feb. 2006; vol. 90; pp. 831-840.
Abel et al.; Fiber-Optic Evanescent Wave Biosensor for the Detection of Oligonucleotides; Anal. Chem.; 1996, vol. 68; pp. 2905-2912.
Stimpson et al; The Utility of Optical Wavegiude DNA Array Hybridization and Melting for Rapid Resolution of Mismatches, and for Detection of Minor Mutant Components in the Presence of a Majority of Wild Type Sequence: Statistical Model and Supporting Data; Genetic Analysis: Biomolecualr Engineering; 1996; vol. 13; pp. 73-80.
U.S. Appl. No. 11/633,980, filed Dec. 4, 2006; Alexander M. Chagovetz; office action issued Oct. 6, 2010.
Heybel et al.; Crucial Role of the Adhesion Layer of the Plasmonic Fluorescence Enhancement; ACS Nano; 2009; pp. 2043-2048; vol. 3, No. 7.
Airola et al; Second-Harmonic Generation from an Array of Subwavelength Metal Apertures; Second-Harmonic-Generation from Subwavelength Metal Apertures; Journal of Optics, A, Pure and Applied Optics, Feb. 1, 2005; pp. s118-s123; vol. 7, No. 2.
Tang et al; C-Shaped Nanoaperture-Inhanced Germanium Photodetector; Optics letters; posted online Feb. 16, 2012; pp. 1519-1521; vol. 31, No. 10.
K. Koerkamp et al; Strong Influence of Hole Shaped Extraordinary Transmission through Periodic Arrays of Subwavelenth Holes; Physical Review Letters; May 1, 2004; vol. 92, No. 18.
U.S. Appl. No. 12/793,883, filed Jun. 4, 2012; Steven M. Blair; office action issued Apr. 5, 2012.
Bishop et al.; Competitive Displacement of DNA During Surface Hybridization; Biophy. J.; Jan. 2007; pp. L10-L12; vol. 91, No. 1.
Guiller et al; Linkers and Cleavage Strategies in Solid-Phase Organic Synthesis and Combinatorial Chemistry; Chem. Rev.; 2000; pp. 2091-2157; vol. 100.
Bauer et al; Biological Applications of High Aspect Ratio Nanoparticles; Journal of Materials Chemistry; Jan. 14, 2004; pp. 517-526; vol. 14.
Murphy et al.; Probing Single-Stranded DNA Conformational Flexibility Using Fluorescence Spectroscopy; Biophysical Journal; Apr. 2004; pp. 2530-2537; vol. 86.
U.S. Appl. No. 12/191,134, filed Aug. 13, 2008; Alexander Chagovetz; office action issued Sep. 9, 2011.
U.S. Appl. No. 12/793,883, filed Jun. 4, 2010; Steven M. Blair; office action dated Nov. 9, 2012.
U.S. Appl. No. 12/603,242, filed Oct. 21, 2009; Steven M. Blair; office action dated Dec. 26, 2012.
U.S. Appl. No. 12/603,242, filed Oct. 21, 2009; Steven M. Blair; office action dated Aug. 23, 2012.
U.S. Appl. No. 12/042,516, filed Mar. 5, 2008; Steven M. Blair; office action dated Oct. 9, 2012.

* cited by examiner

BIOSENSORS INCLUDING METALLIC NANOCAVITIES

RELATED APPLICATIONS UNDER 35 U.S.C. §119(e)

This application claims the benefit of U.S. Provisional Patent Application Ser. No. 60/705,216, filed Aug. 2, 2005, for "BIOSENSORS INCLUDING METALLIC NANOCAVITIES," the entire contents of which are hereby incorporated herein by this reference. This application also claims the benefit of U.S. Provisional Patent Application Ser. No. 60/795,110, filed Apr. 26, 2006, for "METALLIC NANOCAVITIES CONFIGURED TO PROVIDE OPTIMAL RADIATIVE ENHANCEMENT," the entire contents of which are hereby incorporated herein by this reference.

STATEMENT REGARDING FEDERALLY SPONSORED RESEARCH OR DEVELOPMENT

This invention was made in part with Government support under Contract No. ECS-0134548 awarded by National Science Foundation (NSF) and Contract No. 1R21EB000481-01 awarded by National Institute of Health (NIH). The Government has certain rights in this invention.

BACKGROUND OF THE INVENTION

1. Field of the Invention

The invention relates generally to evanescent wave-type biosensors, or biomolecular assays. More specifically, the invention relates to biosensors including substrates with metallic films on one or more surfaces thereof and, in particular, to biosensors with metallic films that include nanocavities with shapes that are configured to optimize the amplification of signals indicative of the presence or amount of one or more analytes present in a sample.

2. Background of Related Art

Plasmonics is the study of phenomena related to the interaction of electromagnetic radiation with an electron gas (or plasma) at a metal surface (B. Schechter "Bright new world," New Scientist 31-33 (2003)). Aside from the now-common surface plasmon resonance (SPR)-based sensors (B. Liedberg, C. Nylander, and I. Lundstrom, "Surface plasmon resonance for gas detection and biosensing," Sen. Actuators, vol. 4, pp. 299-304, 1983; N. Bianchi, C. Rustigliano, M. Tomassetti, G. Feriotto, F. Zorzato, and R. Gambari, "Biosensor technology and surface plasmon resonance for real-time detection of HIV-1 genomic sequences amplified by polymerase chain reaction," Clin. Diagnostic Virology, vol. 8, pp. 199-208, 1997), plasmonics has been applied to molecular detection applications by attaching metallic nanoparticles to molecules for use as light scattering labels (J. Yguerabide and E. E. Yguerabide, "Light-scattering submicroscopic particles as highly fluorescent analogs and their use as tracer labels in clinical and biological applications," Anal. Biochem., vol. 262, no. 2, pp. 157-176, September 1998; T. A. Taton, C. A. Mirkin, and R. L. Letsinger, "Scanometric DNA array detection with nanoparticle probes," Science, vol. 289, pp. 1757-1760, 2000; L. R. Hirsch, J. B. Jackson, A. Lee, N. J. Halas, and J. L. West, "A whole blood immunoassay using gold nanoshells," Anal. Chem., vol. 75, p. 2377, 2003) in biosensing. Nanostructured metallic surfaces have also been studied extensively for surface-enhanced fluorescence (A. Wokaun, H.-P. Lutz, A. P. King, U. P. Wild, and R. R. Ernst, "Energy transfer in surface enhanced luminescence," J. Chem. Phys., vol. 79, no. 1, pp. 509-514, 1983; J. Malicka, I. Gryczynski, Z. Gryczynski, and J. R. Lakowicz, "Effects of fluorophore-to-silver distance on the emission of cyanine-dye-labeled oligonucleotides," Anal. Biochem., vol. 315, pp. 57-66, 2003) and Raman scattering (SERS) (K. Kneipp, H. Kneipp, R. Manoharan, E. B. Hanlon, I. Itzkan, R. R. Dasari, and M. S. Feld, "Extremely large enhancement factors in surface-enhanced Raman scattering for molecules on colloidal gold clusters," Appl. Spectros., vol. 52, pp. 1493-1497, 1998). One of the major drawbacks of these surface-enhanced techniques is that the nanostructure is disordered (but sometimes with fractal order) such that the fluorescence or Raman enhancement factors are spatially-varying, as evidenced by "hot-spots" on the surface (V. M. Shalaev, R. Botet, J. Mercer, and E. B. Stechel, "Optical properties of self-affine thin films," Phys. Rev. B, vol. 54, pp. 8235-8242, 1996). The hot-spot effect may render these techniques unsuitable for quantitative assays, especially in an array format, as the average enhancement over a defined sensing zone may not be very high, and the enhancement from zone to zone may vary. As a result, there have been efforts in which molecules are attached to lithographically defined arrays of metallic nanoparticles (H. Ditlbacher, N. Felidj, J. R. Krenn, B. Lambprecht, A. Leitner, and F. R. Aussenegg, "Electromagnetic interaction of fluorophores with designed 2D silver nanoparticle arrays," Appl. Phys. B, vol. 73, p. 373, 2001; N. Felidj, J. Aubard, G. Levi, J. R. Krenn, A. Hohenau, G. Schider, A. Leitner, and F. R. Aussenegg, "Optimized surface-enhanced Raman scattering on gold nanoparticle arrays," Appl. Phys. Lett., vol. 82, no. 18, pp. 3095-3097, 2003). With these architectures, uniformity in nanoparticle size, shape, and spacing result in well-defined enhancement in terms of magnitude and spatial location. However, these techniques do not provide complete isolation from background produced by unbound species, as uniform illumination can excite fluorescence from molecules located between nanoparticles, which produce background signals at the detector.

An important recent advance is the demonstration of extraordinary light transmission through a periodic array of subwavelength metallic apertures (T. W. Ebbeson, H. J. Lezec, H. F. Ghaemi, T. Thio, and P. A. Wolff, "Extraordinary optical transmission through sub-wavelength hole arrays," Nature, vol. 391, pp. 667-669, 1998) or nanocavities, where, in the absence of the nanocavities, no light passes through the metal film. Even though this has been quite an active area of research, some disagreement about the origin of the transmission enhancement still exists (H. J. Lezec and T. Thio, "Diffracted evanescent wave model for enhanced and suppressed optical transmission through subwavelength hole arrays," Optics Express, vol. 12, no. 16, pp. 3629-3651, 2004). However, it is generally believed (I. Avrutsky, Y. Zhao, and V. Kochergin, "Surface-plasmon-assisted resonant tunneling of light through a periodically corrugated thin metal film," Opt. Lett., vol. 25, pp. 595-597, 2000; A. K. Sarychev, V. A. Podolsky, A. M. Dykhne, and V. M. Shalaev, "Resonance transmittance through a metal film with subwavelength holes," IEEE J. Quantum Electron., vol. 38, pp. 956-963, 2002; L. Martin-Moreno and F. J. Garcia-Vidal, "Theory of extraordinary optical transmission through subwavelength hole arrays," Opt. Express, vol. 12, pp. 3619-3628, 2004.5) that the periodic array of nanocavities acts as a two-dimensional diffraction grating, which, at specific incidence angles, allows light to couple from free space into surface plasmon polariton (SPP) Bloch modes on either metal interface. These SPP modes can constructively interfere within the nanocavities, resulting in intensity enhancement (H. J. Lezec and T. Thio, "Diffracted evanescent wave model for enhanced and suppressed optical transmission through subwavelength hole arrays," *Optics Express*, vol. 12, no. 16, pp. 3629-3651, 2004) and, therefore, greater transmission. The inventors have demonstrated experimentally, using fluorophores as local intensity probes, that light is indeed localized within the nanocavities (Y. Liu and S. Blair, "Fluorescence enhancement from an array of subwavelength metal apertures," *Opt. Lett.*, vol. 28, pp. 507-509, 2003) and that enhanced fluorescence transduction can be performed (Y. Liu, J. Bishop, L. Williams, S. Blair, and J. N. Herron, "Biosensing based upon molecular confinement in metallic nanocavity arrays," *Nanotechnology*, vol. 15, pp. 1368-1374, 2004; Y. Liu and S. Blair, "Fluorescence transmission through 1-D and 2-D periodic metal films," *Opt. Express*, vol. 12, no. 16, pp. 3686-3693, 2004).

More recently, enhancement in single molecule fluorescence h as been reported for round (H. Rigneault, J. Capoulade, J. Ditinger, J. Wenger, N. Bonod, E. Popov, T. W. Ebbesen, and P.-F. Lenne, "Enhancement of single-molecule fluorescence detection in subwavelength apertures," Physical Review Letters 95, 117401 (2005)) and rectangular (J. Wenger, P.-F. Lenne, E. Popov, H. Rigneault, J. Ditinger, and T. W. Ebbesen, "Single-molecule fluorescence in rectangular nano-apertures," Optics Express 13, 7035-7044 (2005)) nanoapertures, and a computational model for radiative enhancement has been developed (Y. Liu, F. Mandavi, and S. Blair, "Enhanced fluorescence transduction properties of metallic nanocavity arrays," IEEE Journal of Selected Topics in Quantum Electronics 11, 778-784 (2005)).

Multi-analyte, or array, biosensing is an increasingly important area of research and development for many clinical, environmental, and industrial applications. In the clinical application of genetic screening, for example, high sensitivity hybridization arrays are needed for rapid identification of genetic disorders in the presence of multiple genotypes or mutations (B. J. Maron, J. H. Moller, C. E. Seidman, G. M. Vincent, H. C. Dietz, A. J. Moss, H. M. Sondheimer, R. E. Pyeritz, G. McGee, and A. E. Epstein, "Impact of laboratory molecular diagnosis on contemporary diagnostic criteria for genetically transmitted cardiovascular diseases: hypertrophic cardiomyopathy, long-QT syndrome, and Marfan syndrome," Circulation 98, 1460-1471 (1998); J. G. Hacia "Resequencing and mutational analysis using oligonucleotide microarrays," Nature Genetics 21, 42-47 (1999)).

However, many challenges, such as improving sensitivity, accuracy, precision and specificity of the assays, reducing assay time, etc., remain in the field.

SUMMARY OF THE INVENTION

A biomolecular assay includes a substrate with a metallic film, or layer, on at least one surface thereof. The metallic film includes nanocavities. The nanocavities are configured to enhance signals that are representative of the presence or amount of one or more analytes (e.g., proteins or peptides, nucleic acids, small molecule ligands, ions, etc.) in a sample or sample solution. Such a biomolecular assay may be used for a variety of purposes, including, without limitations, receptor-ligand binding, drug screening, real-time nucleic acid hybridization, clinical diagnostics, etc.

A biomolecular assay may be fabricated by forming a substrate, or support, from a suitable material (e.g., glass, quartz, another optically suitable (e.g., transparent) inorganic material, an optical plastic, a combination of any of the foregoing (as is the case in so-called "thin-film" waveguides, which include multiple layers), etc.). A metallic film, or layer, is applied to at least one surface of the substrate (e.g., by deposition techniques, lamination processes, etc.). By way of nonlimiting example, the metallic film may have a thickness of about 100 nm.

Nanocavities are formed in the metallic film by suitable processes (e.g., mask and lift-off processes (such as those used in semiconductor device fabrication), mask and etch processes (such as those used in semiconductor device fabrication), with a laser, etc.). The nanocavities may extend completely through the metallic film, with the underlying substrate being exposed therethrough. A lateral dimension (e.g., diameter) of each nanocavity may be about the same as the thickness of the metallic layer, although lateral nanocavity dimensions may differ from the thickness of the metallic layer.

Nanocavities of virtually any shape may be formed. Examples of nanocavity shapes include, but are not limited to, round (e.g., circular, oval, elliptical, egg-shaped, etc.), quadrilateral (e.g., square, rectangular, parallelogram, trapezoidal, etc.), triangular, and other polygonal shapes. The nanocavities that are formed in a metallic film may all have substantially the same shapes and dimensions, or a variety of shapes and/or dimensions of nanocavities may be included in the metallic film of a biomolecular assay that incorporates teachings of the invention.

The nanocavities may be arranged in such a way that facilitates the coupling of incident light into surface modes, or waves, on the metallic film, which surface modes can constructively interfere within the nanocavities. For example, when incident light is to be directed from the substrate, or back side of the biomolecular assay, and fluorescence is to be detected at a location adjacent to the opposite, top surface of the biomolecular assay (i.e., the surface by which the metallic film is carried), the metallic film prevents excitation of fluorophores in the bulk solution, which is located over the metallic substrate. As another example, when incident light is directed toward the biomolecular assay from a location over the metallic film and detection occurs at a location adjacent to the back side of the substrate, although marker molecules that remain within solution may undergo a change in state (e.g., fluorescence by fluorescent marker molecules), the marker molecules that remain in solution over the metallic film remain substantially undetected. This is because light emitted from a location above the metallic film does not pass through the metallic film and since the size of each nanocavity may be too small for fluorescent light emitted from locations over the surface of the metallic film to pass therethrough. Fluorescent light generated within the nanocavities does exit the nanocavities, however, and is enhanced by the materials from which the nanocavities are formed, as well as by the configurations and dimensions of the nanocavities.

In specific applications, however, fluorescence signals originating from fluorescent species lying outside of the cavity may be a concern. For example, these signals may increase background or noise of an assay and thus compromise the sensitivity and/or precision of the assay. Partial or complete isolation of fluorescence signals originating from fluorescent species lying outside of the cavity can be obtained by either narrowing the fluorescence collection angle or by passivating the surfaces of the metallic film.

The shapes of the nanocavities may be configured to optimize signal amplification. It has been discovered that nanocavities of a variety of shapes, including circular, square, and triangular, provide a good degree of radiative, or signal, enhancement, depending upon the dimensions (e.g., diameters of circular nanocavities, edge lengths of square and triangular nanocavities, etc.) of the nanocavities. Square nanocavities may provide better signal enhancement than circular nanocavities, while triangular nanocavities may provide even greater signal enhancement. Without limiting the scope of the invention, circular nanocavities formed in a gold film having a thickness of about 100 nm may enhance a signal by up to about 1.8 times (for nanocavities having diameters of about 160 nm), square nanocavities formed in a gold film having a thickness of about 100 nm may enhance a signal by up to about 2.1 or 2.2 times (for nanocavities with edges of about 125 nm in length and 20 nm radius corners), and equilateral triangular cavities formed in a gold film having a thickness of about 100 nm may enhance a signal by up to about 3 times (for nanocavities with edges that are about 175 nm long an that have 20 nm radius corners). It is believed that even greater radiative, or signal, enhancements may be achieved by further tailoring the shapes or dimensions of nanocavities.

Optionally, a biomolecular substrate according to the invention may include one or more transparent films positioned between the substrate and the metallic film or over the metallic film for directing incident light to the nanocavities. Nanocavities may extend into or through such transparent films.

Surfaces of the biomolecular substrate may be passivated to prevent capture molecules (e.g., bait molecules) from adhering, or being immobilized, to undesired locations thereof. The surfaces of the metallic film may be passivated, for example, with polyethylene glycol (PEG)-thiol, another metal (e.g., gold)-selective thiol molecule, or any other material that prevents capture molecules from being immobilized to the metallic film, or reduce immobilization of capture molecules to the metallic film. Thus, the capture molecules are instead immobilized to the surface of the substrate exposed to and located within or adjacent to the nanocavities. Alternatively, the exposed surfaces of the substrate may be passivated (e.g., with PEG silane) to prevent capture molecules from adhering to the substrate and, rather, causing the capture molecules to be immobilized only to the metallic surfaces. As another alternative, a major surface of the metallic film may be covered with a coating film (e.g., another transparent film), and the exposed surfaces of the coating film, as well as surfaces of the substrate that are exposed through the coating film and the metallic film, may be passivated, causing capture molecules to adhere only to the unpassivated exposed edges of the metallic film, which form part of the surface of each nanocavity.

The biomolecular substrate may be configured in such a way that surface modes (e.g., surface plasmons, which generate an evanescent field) may be generated at the surface of the metallic film or at the portions of the surface of the substrate that are exposed by the nanocavities. These surface modes may provide enhanced excitation of marker molecules on analyte that has been bound to capture molecules within the nanocavities, particularly surface modes that constructively interfere with one another.

Capture molecules are introduced into the nanocavities and immobilized to surfaces of the nanocavities, the substrate, or both, as known in the art. The capture molecules are specific for one or more analytes of interest.

Increased surface area structures, such as corrugated patterning having a "bullseye" configuration, other patterns, or the like may be formed around each nanocavity.

Nanocavities may be arranged in nanostructure architectures such as a periodic array of nanocavities, a random array of nanocavities, and "bullseye" structure of single nanocavity surrounded by an annular, corrugated grating. Several embodiments of nanostructure architectures are illustrated in FIG. 1 as described herein.

A periodic array of metallic nanoparticles can also provide enhanced signals, since, in essence, metallic nanoparticles merge to form a periodic hole array. An example of a nanoparticle array is illustrated in FIG. 1 (c) as described herein.

Such a biomolecular assay may include a sequential delivery system, in which a sample flows into the nanocavities in sequence. Sequential delivery systems are useful for detecting small concentrations of analyte, as well as with samples having small volumes. Of course, other types of delivery systems, including delivery systems with sections through which portions of a sample may flow in parallel, are also within the scope of the invention.

Once a sample has traveled through the delivery system, it may be recycled through the system one or more times. Recycling may be effected in a loop, in which the sample travels through the system in the same direction each time, or may be effected by reversing the direction in which the sample flows through the delivery system. Recycling may be useful for optimizing detection of low analyte concentrations in a sample or for detecting analyte in samples having small volumes.

Sample flow through a sequential or any other configuration of delivery system may be effected by mechanisms that are fabricated on or assembled with the biomolecular assay. Examples of flow facilitators include, but are not limited to, peristaltic pumps, positive pressure systems, and negative pressure systems.

Mixing structures, such as those disclosed in U.S. patent application Ser. No. 10/350,361, filed on Jan. 23, 2003, the disclosure of which is hereby incorporated herein, in its entirety, by this reference. Such mixing structures may also be included in a sample delivery system of a biomolecular assay that incorporates or may use the invention to advantage. In addition or as an alternative to being located at reaction sites of the biomolecular assay, mixing structures may be positioned along other locations of the sample delivery system, including between reaction sites and at ends of the system, where they may increase the homogeneity of a sample prior to recirculating the sample through the delivery system.

The use of a sequential delivery system, sample recirculation, sample flow facilitation, sample mixing, or any combination thereof may reduce the amount of reagent required for detecting an analyte in a sample.

As a nonlimiting example, the biomolecular assay may be used in an assay system or technique that employs fluorescence detection techniques. Such a system also includes a source of electromagnetic radiation and a detector. The source is configured to emit electromagnetic radiation of one or more wavelengths, or "incident light," that excites fluorescent dye molecules that are to be used in the system, and oriented to direct the radiation onto the nanocavities or into the substrate. The incident light may be in the form of light transmitted from a source, an evanescent field generated as light is directed into and internally reflected within a substrate or transparent film that comprises a waveguide, or a combination thereof. Radiation can penetrate the nanocavities directly and, optionally, due to constructive interference that may occur because of the arrangement of the nanocavities, thereby exciting species within the nanocavities, or radiation may be internally reflected within the substrate, generating an evanescent field at one or more surfaces thereof. The incident light excites fluorescent dye molecules that are immobilized (directly or indirectly, depending upon the assay binding technique (e.g., a sandwich-type assay, a binding competition assay, etc.) employed relative to capture molecules within the nanocavities. Fluorescent dye molecules within the nanocavities are excited and, thus, emit electromagnetic radiation. The electromagnetic radiation is enhanced by the nanocavities and the metallic substrate. It is then detected by the detector. An aperture associated with the detector may tailor the angle of a collection cone of radiation emitted by the fluorescent dye molecules.

A biomolecular assay that incorporates teachings of the invention may be used with known mass detection processes.

As an example, a reference analyte of known concentration and analyte within a sample, which has an unknown concentration, may be labeled with different marker molecules (e.g., fluorescent molecules that emit different wavelengths, or colors, of light) and their binding to capture molecules that have been immobilized within the nanocavities compared to provide an indication of the amount of analyte in the sample. The affinities of the reference analyte and the sample analyte for the capture molecule, which may be known, may be the same or different.

Of course, systems and techniques that employ chemiluminescence, photoluminescence, electroluminescence, and other types (i.e., no fluorescent) of marker molecules (e.g., metallic markers, such as the gold markers used in Raman scattering techniques, etc.) are also within the scope of the invention.

Other features and advantages of the invention will become apparent to those of ordinary skill in the art though consideration of the ensuing description, the accompanying figures, and the appended claims.

DETAILED DESCRIPTION

The invention includes biosensors comprising metallic nanocavities, thereby providing an apparatus, elements of an apparatus and methods of fabrication and using such an apparatus. In the following description, reference is made to the accompanying drawings, which show, by way of illustration, several embodiments of the invention.

Figure 2:
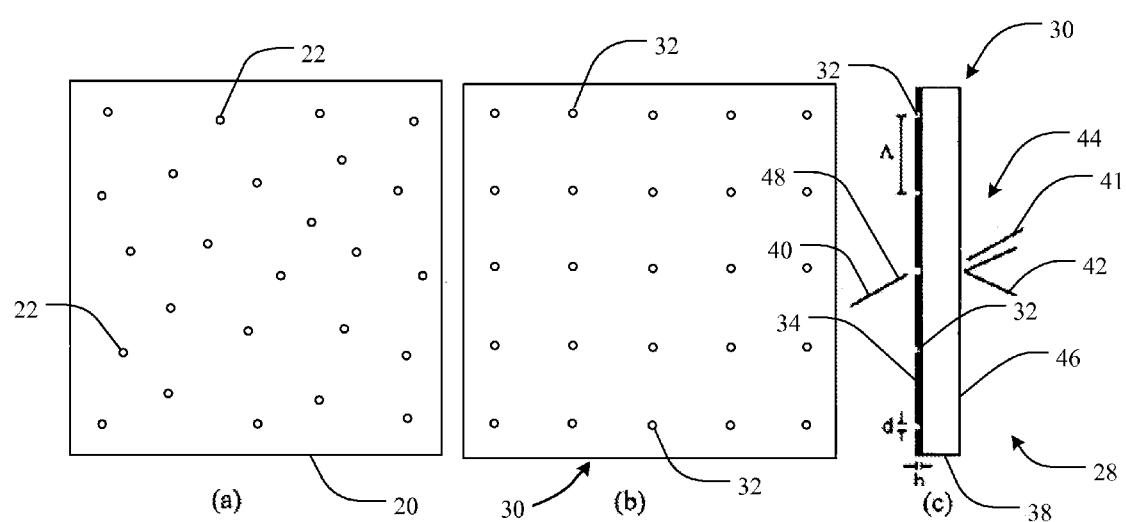
FIG. 2 schematically depicts: (a) a plan view of a random nanocavity (20, 22) (b) a plan view of a periodic nanocavity array (30, 32); and (c) a side view of the periodic nanocavity array of FIG. 2(b) (28, 30, 32, 34, 38, 40, 41, 42, 44, 46, 48).

FIG. 2 (a) and (b) illustrate a randomly arranged array 20 and a periodic arranged array 30 of nanocavities, 22 and 32, respectively. FIG. 2 (c) illustrates a cross section 28 of FIG. 2(b) shown formed on a metallic layer 34 (indicated by solid black rectangles) on a surface 36 of a quartz substrate 38. FIG. 2 (c) also shows optical paths 40, 41 and 42, and geometrical parameters d and Λ of the nanocavities, where d is the nanocavity diameter and Λ is the spacing of adjacent nanocavities. As illustrated in FIG. 2 (c), when incident light 40 is directed toward the nanocavities 32 from a location 48 over the metallic layer 34, enhanced fluorescence output of fluorescent molecules within the nanocavities 32 may be detected at a location 44 adjacent to a back side 46 of the substrate 38. For example, fluorescence output of fluorescent molecules within nanocavities may be read out using standard fluorescence scanners (i.e., normal incidence excitation, normal incidence fluorescence collection) from the backside 46 of the substrate. However, fluorescence output may also be detected in a reflection mode rather than a transmission mode as described herein.

Figure 1:
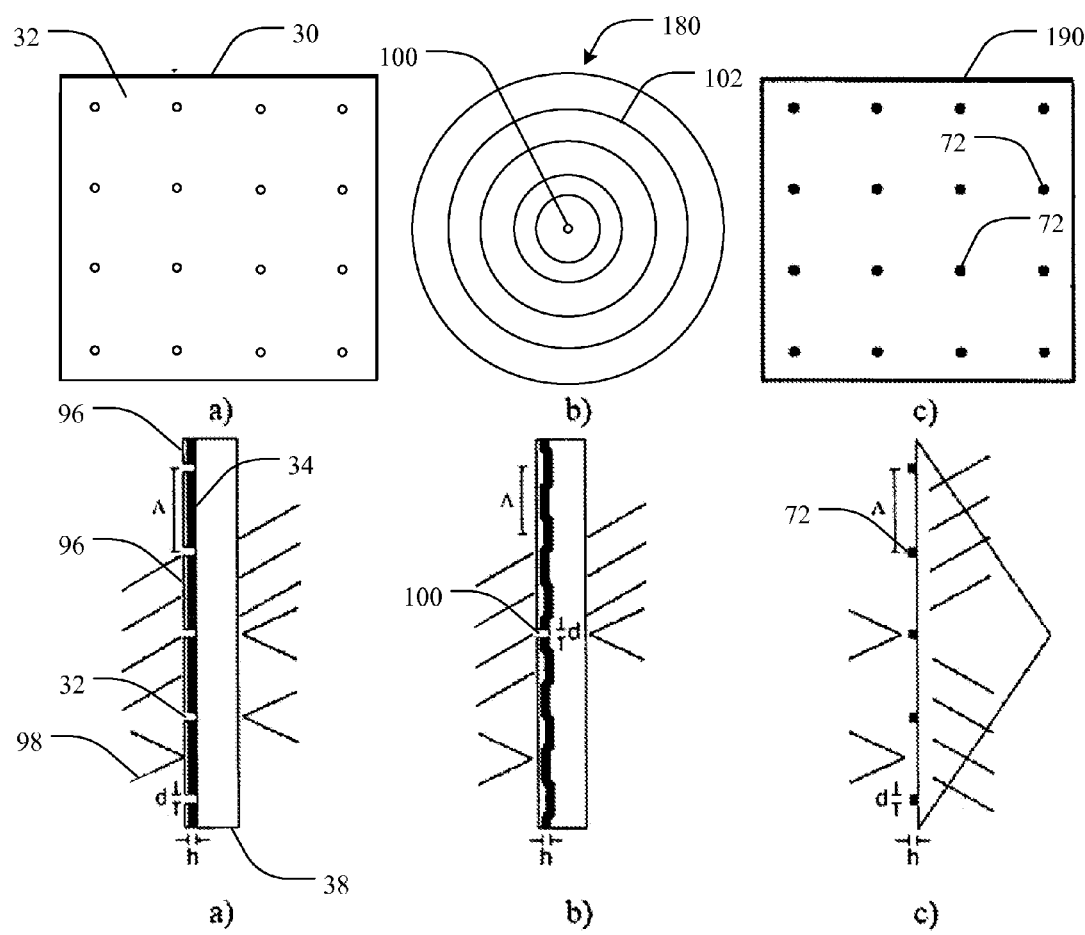
FIG. 1 schematically depicts (in plan and cross section views) examples of periodic metallic nanostructure architectures, including: (a) a periodic array of nanocavities (30, 32, 34, 38, 96, 98, 100); (b) a "bullseye" structure of a single nanocavity surrounded by an annular, corrugated grating (100, 102, 180); and (c) a periodic array of nanoparticles (72, 90).
Figure 3:
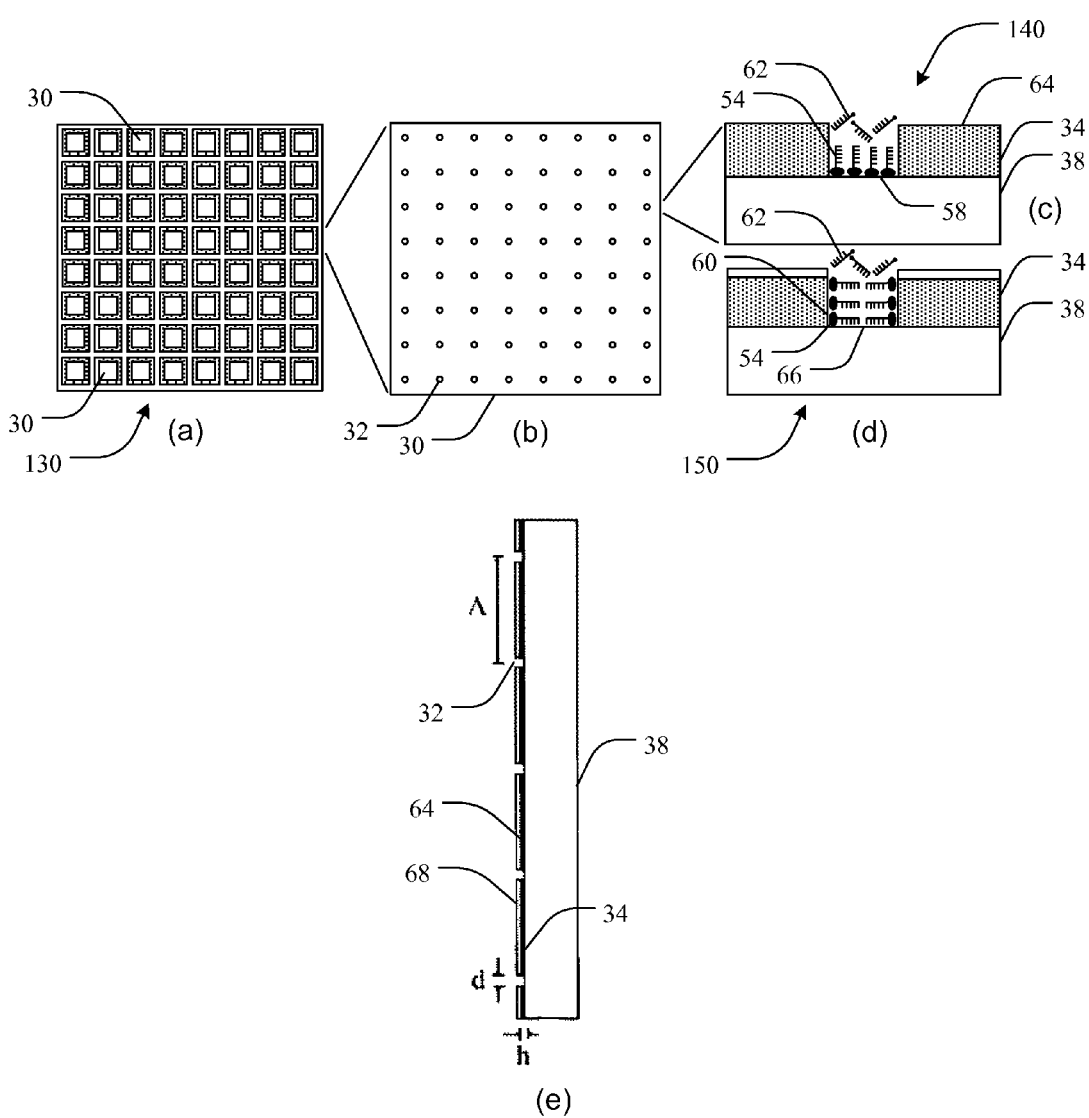
FIG. 3 illustrates a hybridization array (30, 32, 34, 38, 54, 58, 60, 63, 64, 66, 68, 130, 140, 150), where each hybridization zone includes an array of metallic nanocavities. Two nanocavity embodiments are also illustrated: Type I, where the probe molecules are selectively attached to the bottoms of the nanocavities, and Type II, where the probe molecules are selectively attached to the sidewalls of the nanocavities. The illustrations are not to scale.

Target or capture molecules of an assay may reside on the sidewalls, the bottom surfaces, or both the sidewalls and the bottom surfaces of the nanocavities. Two nanocavity embodiments are illustrated in FIG. 3: Type I (as shown in FIG. 3 (c)), where capture molecules 54 (e.g., probe oligonucleotides) are selectively attached to the bottoms 58 of the nanocavities, and Type II (as shown in FIG. 3 (d)), where the probes 54 are selectively attached to the sidewalls 60 of the nanocavities. As shown in FIG. 3(a), a hybridization array 130 comprises one or more sub-arrays or periodic array 30 of metallic nanocavities within which capture, or probe, oligonucleotides 54 are tethered directly to the nanocavities 32. One molecular species 62 (i.e., the target oligonucleotides or analyte, which is fluorescently labeled) specifically bind to the capture oligonucleotides 54 through hybridization. An optically-transduced, real-time signal in proportion to the number of bound target oligonucleotides are detected from the side of the sensor array opposite to the side on which the sample solution is introduced, thereby providing isolation from unbound species, which may represent a significant fraction of the detected signal in a washless assay. In this nanocavity array architecture, fluorescence from unbound species 98, as shown in FIG. 1 (a), do not penetrate the opaque metal except at the nanocavities. By measuring the hybridization kinetics in real-time, non-specific binding may be factored out as well. Study of fluorescence enhancements using the two embodiments also allows for independent and direct measurement of enhancement factors for molecules located at the bottom surfaces (Type I) and at the sidewalls (Type II).

However, fluorophores placed in close proximity to the exposed metal surface of a periodic nanocavity structure may couple to surface plasmons and emit from the back side of the substrate at specific angles. Isolation from this fluorescence signal may be obtained by either narrowing the collection angle to exclude this contribution or by passivating the surfaces of the metallic film.

To prevent capture molecules from binding to undesired locations of the nanocavities, the surfaces of the metallic film or the surface of the substrate may be passivated. For example, for Type I nanocavities (FIG. 3 (c)), a surfaces 64 of the metallic film 34 may be passivated with polyethylene glycol (PEG)-thiol. Thus, the probe oligonucleotides (i.e., capture molecules) are selectively attached to the bottoms of the nanocavities 32. On the other hand, for Type II nanocavities (FIG. 3 (d)), the exposed surface 66 of the substrate 38 may be passivated (e.g., with PEG silane) to prevent capture molecules 54 from adhering to the surface 66 of the substrate 38 and, rather, causing the capture molecules 54 to be selectively attached to the sidewalls 60 of the nanocavities. Alternatively, as shown in FIG. 3 (e), to facilitate coupling of the capture molecules 54 to the sidewalls 60 of the nanocavities, a thin (~20 nm) layer 68 of $SiO_2$ is deposited to cover the top metal surface 64. With this structure, the only exposed substrate surface is the inside walls of the nanocavities, to which selective derivatization of capture molecules is performed. A layer (e.g., ~5 nm) of Al or Cr, which is not shown in FIG. 3 (e), may be used to promote adhesion of the $SiO_2$ layer.

Surfaces of nanocavity substrates may also be modified for covalent or noncovalent immobilization of capture molecules. For example, $SiO_2$ and $Si_3N_4$ surfaces of nanocavity substrates may be modified with a reactive species, e.g., epoxysilane. After surface modification with a reactive species, coating of the capture molecules may be performed. For example, amine-modified nucleic acid probes may be spotted on epoxysilane-modified surfaces, and reactions of the amine groups and the epoxy groups cause the amine-modified nucleic acid probes covalently linked to the surface of the substrate.

Not wishing to be bound by theory, the surface plasmon modes at each of the metal interfaces in general have different propagation constants, such that usually only one of these modes (the one at the metal-air interface) plays a role in enhanced transmission. However, the modes at the two interfaces may be coupled together. Fluorescence excitation enhancement may be improved by surface plasmon cross-coupling. Surface plasmon cross-coupling may be achieved by controlling the refractive index at the substrate by depositing a thin film of silicon oxynitride (SiON) between the metallic film and quartz substrate. FIG. 1 (a) shows a SiON layer 96 deposited on the metallic surface 34. For example, with SiON deposited by plasma-enhanced chemical vapor deposition, one can have continuous control over refractive index in the range 1.46 to 2.05 by adjusting the relative ratio of oxygen and nitrogen atoms. For Type II nanocavities as shown in FIG. 3 (d), the effects of the finite thickness of $SiO_2$ on the top surface should also be taken into account in the propagation constant of the surface plasmon wave at that interface.

Nanocavity geometry also has a strong influence on the emission properties of the fluors within a nanocavity, most likely based upon the nanocavity aspect ratio h/d, where h is the height or depth of the nanocavity. Geometric properties, such as spacing Λ and the incident angle of the incident light, may also be optimized to maximize surface plasmon coupling.

Figure 4:
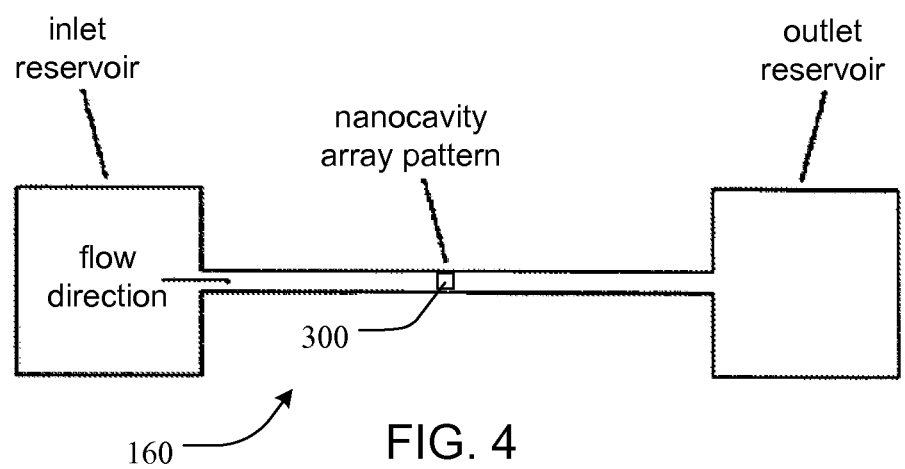
FIG. 4 depicts an example of microfluidic channels (160) that may be used in a time hybridization experiment (300).

A sample may be delivered to the array of hybridization zones through a flow cell or a microfluidic channel. As shown in FIG. 4, a nanocavity array 300 is placed within a microfluidic channel 160. Sample flow is produced by a syringe pump with suitable a flow rate, e.g., of 0.3 mL/min. In order to avoid binding of target to the inside surface of the channels, the interior surface area of the channels may be passivated, e.g., with bovine serum albumin (BSA).

Sub-arrays of metallic nanostructures may provide highly sensitive, real-time detection. Three periodic metallic nanostructures are shown schematically in FIG. 1. FIG. 1 (a) through (c) illustrate a periodic array 30 of nanocavities, a so-called "bullseye" structure 180 and a modified periodic array 190 of nanoparticles. The structure 180 being of single nanocavity 100 surrounded by an annular, corrugated grating 102. Cross sections corresponding to the respective nanostructures, showing geometrical parameters and optical paths, are also respectively shown in FIG. 1.

In the first two architectures (FIG. 1 (a) and (b)), the nanocavities 32 serve as the binding and detection sites of a target entity, and in the third architecture (FIG. 1 (c)), the nanoparticles 72 serve as the binding and detection sites. Enhanced fluorescence transduction occurs through the optical excitation of molecules preferentially bound within metallic nanocavities or attached to metallic nanoparticles.

Not wishing to be bound by theory, enhanced fluorescence of the three nanostructures of FIG. 1 occurs through two mechanisms—increased fluor excitation through the coupling of incident light with surface Plasmon modes (where the coupling occurs through the diffraction grating produced by the periodic patterning of the metal in the nanocavity architectures and by direct excitation of the local plasmon resonance of the nanoparticles) and interaction of the fluors with the metallic nanostructure (either by confinement within a metallic nanocavity or by proximity to a metallic nanoparticle) resulting in increased fluorescence yield. These enhancement mechanisms may produce more than an order of magnitude increase in fluorescence as compared to direct excitation on a transparent substrate.

Individual nanocavities have localized surface plasmon resonances that can undergo spectral shift upon change in the dielectric properties of the enclosed environment (i.e., target binding); when placed in specific spatial arrangements, collective oscillations can produce a narrower resonance. A measurable change in the position of the resonance peak can be obtained upon molecular binding within nanocavities. The spectral position of the resonance peak changes based upon the dielectric environment of the nanocavities. This label-free microarray detection target molecules may be achieved by using a conventional two-color scanner to measure the resonance shift in reflection upon molecular binding.

Nanocavity arrays significantly improve the signal to background ratio. Accordingly, nanocavity arrays can find great uses in many clinical, environmental, and industrial applications, thus offer fast, sensitive, real-time detection of target entities.

In typical real-time hybridization arrays (which are generally based upon evanescent wave excitation at a planar surface), excitation light covers the entire sensing zone area (as well as the entire array of zones), across which the probe molecules are spread uniformly. When bound target surface concentration is low (as it can be well before the end point of the hybridization kinetic reaction occurs or even at the end point for low concentration species), much of the excitation light is wasted, or, even worse, induces background signal from solvent or unbound species lying within the evanescent field. Without wishing to be bound by theory, real-time hybridization arrays, where the sensing zones are based upon sub-arrays of metallic nanostructures, solve this problem by two mechanisms: via selective surface chemistry, target molecules only bind to the nanostructures, about which excitation and emission enhancement of fluorescence occurs (by a total factor $M_{tot}$); and the fill fraction η over which these enhancements occur is less than 100%, thereby providing isolation from sources of background fluorescence. These factors are nearly identical to the advantages that confocal and near-field techniques offer in single-molecule fluorescence microscopy (W. E. Moerner and D. P. Fromm, "Methods of single-molecule fluorescence spectroscopy and microscopy," Review of Scientific Instruments 74, 3597-3619 (2003)), except that the nanoscopic detection sites are fixed (and arranged in subarrays within a detection zone) and the molecules of interest diffuse to the detection sites where they bind.

Arrays of metallic nanocavities may be used in clinical diagnostics, where a particular area of need is to improve the ability to rapidly determine the identity of pathogens responsible for a given infection. With respect to identification, there are clinical scenarios where similar signs and symptoms can result from infection by any of a multitude of pathogens, including viruses, bacteria and, in some instances, fungi. A common clinical example is pneumonia, where it would be desirable to test for up to ten different viruses and bacteria (e.g., *Streptococcus pneumoniae, Influenza*, etc.).

Another clinical example where multiple organisms can be causative is sepsis wherein a pathogen(s) is proliferating in the bloodstream. Currently, the mainstay technology of pathogen identification remains culture of the organism followed by identification by biochemical means (for bacteria) or staining with antibodies (for viruses or bacteria). Culture and identification of bacteria typically requires two or more days and virus culture can take one to several weeks. Significant advances with regard to reducing identification times have been achieved by nucleic acid amplification methods, notably the polymerase chain reaction (PCR). For many viruses and some bacteria, identification times have been reduced to less than one day. However, PCR methods in their current format remain limited in terms of their ability to simultaneously detect more than 6-8 pathogens. This limitation is due to the technical challenges associated with multiplexing PCR and a limited number of sufficiently spectrally distinct detection fluors that can be bound to oligonucleotide probes. In this context, there is substantial interest in and effort directed towards exploiting array based technologies wherein amplification technologies, such as PCR, are used to multiplex amplify various signature genetic regions from suspected pathogens followed by hybridization of the amplification products to an array containing complementary sequences. While technically attractive, a current bottleneck remains the length of hybridization time required to achieve sufficient signal above background, with most arrays requiring hybridization times on the order of hours to overnight (Y. Y. Belosludtsev, D. Boweman, R. Weil, N. Marthandan, R. Balog, K. Luebke, J. Lawson, S. A. Johnston, C. R. Lyons, K. O'Brien, H. R. Garner, and T. F. Powdrill, "Organism identification using a genome sequence independent universal microarray probe set," Biotechniques 37, 654-660 (2004)).

Ideally, with infectious disease, physicians would like the result of pathogen identification within 2 hours of sample collection. There are three steps in molecular diagnostics: 1) sample preparation, 2) PCR, and 3) detection. Sample preparation takes roughly 15-30 minutes, while PCR can be performed in 30-60 minutes. In the case of infectious disease, this leaves roughly 30-75 minutes for detection, which is clearly not possible with current hybridization arrays. Nanocavity arrays as hybridization zones may provide fast and sensitive detection of multiple pathogens.

Another example of an application for nanocavity arrays is gene expression analysis (H. P. Saluz, J. Iqbal, G. V. Limmon, A. Ruryk, and W. Zhihao, "Fundamentals of DNA-chip/array technology for comparative gene-expression analysis," Current Science 83, 829-833 (2002)). With their increased sensitivity (owing to real-time analysis and greatly improved signal to background ratio), nanostructure hybridization arrays can facilitate a new scientific avenue in expression analysis through the detection of less abundantly expressed genes, which currently cannot be studied by using endpoint or other real-time methods. This new capability could ultimately lead to better understanding of regulatory pathways, drug intervention, and the biological behavior of tumor cells, for example. Another avenue lies in the ability to analyze RNA populations directly (where even linear amplification steps can either be avoided entirely or minimized) where end-labeling of RNA would occur after a digestion step to cleave the native RNA to 20 to 100 bases; cleaving is performed to enhance the hybridization kinetics via increased diffusion.

Low-cost nanofabrication techniques can be applied such that the cost of producing the array itself may be no greater than the cost of producing a compact disc. For real time array analysis, low-cost and disposable microfluidic flow cells may be attached to the array in a hybridization unit, which can be compactly integrated with external optical excitation and parallel readout using imaging optics and a low-noise charge-coupled device camera or other suitable device. The coupling of excitation light is straightforward (comparable to the methods used in SPR biosensors), as a broad beam of light covers the entire array and the coupling is relatively insensitive to angle and wavelength (as opposed to standard SPR).

The invention is further described in the following non-limiting examples, which are offered by way of illustration and are not intended to limit the invention in any manner.

EXAMPLES

1. Biosensing Based Upon Molecular Confinement in Metallic Nanocavity Arrays

Liu et al. (Y. Liu, J. Bishop, L. Williams, S. Blair, and J. N. Herron, "Biosensing based upon molecular confinement in metallic nanocavity arrays," *Nanotechnology*, vol. 15, pp. 1368-1374, 2004) describes the basis for an affinity biosensor platform in which enhanced fluorescence transduction occurs through the optical excitation of molecules located within metallic nanocavities. The contents of Liu et al. are hereby incorporated herein, in their entireties, by this reference. The nanocavities of Liu et al. are about 200 nm in diameter, are arranged in periodic or random two-dimensional arrays, and are fabricated in 70 nm thick gold films by e-beam lithography using negative e-beam resist. It has been shown that both periodic and randomly placed metallic nanocavities can be used to enhance the fluorescence output of molecules within the cavities by about a factor of ten. In addition, the platform provides isolation from fluorescence produced by unbound species, making it suitable for real-time detection, for example, real-time detection of 20-base oligonucleotides in solution.

2. Enhanced Fluorescence Transduction Properties of Metallic Nanocavity Arrays

Liu et al. (Y. Liu, F. Mandavi, and S. Blair "Enhanced fluorescence transduction properties of metallic nanocavity arrays," IEEE Journal of Selected Topics in Quantum Electronics 11, 778-784 (2005)) describes fluorescence enhancement of molecular species bound within metallic nanocavities. The contents of Liu et al. are hereby incorporated herein, in their entireties, by this reference. The nanocavity structures of Liu et al. possess a number of desirable properties for real-time microarrays, such as localization of excitation light within the nanocavities, strong isolation from fluorescence produced by unbound species, and an apparent increase in fluorescence yield for bound species. Experimental measurements show nearly a factor of two increase in excitation intensity within the nanocavities, and factor of six increase in yield. An electromagnetic model of a dipole within a nanocavity shows an increase in radiative output consistent with estimated yield, and also verifies the strong fluorescence isolation from species lying outside the nanocavity.

3. Biosensing Based Upon Molecular Confinement in an Array of Metallic Nanocavities The following study is designed to optimize and validate a hybridization array platform based upon sub-arrays of metallic nanocavities. These nanocavity arrays are conducive to real-time measurement of hybridization kinetics, are scalable to large hybridization array formats, and possess significantly improved molecular sensitivities to enable rapid screenings in a clinical setting.

To determine molecular sensitivity in a real-time assay, derivatization of the nanocavities either occurs at the bottom (quartz) surface or at the gold sidewall to avoid the binding of species in solution to the top surface. Therefore, two nanocavity array embodiments are studied for selective derivatization of either the exposed quartz surface or the nanocavity sidewall. The first embodiment (Type I) is shown schematically in FIG. 3 (c). These samples are passivated with mPEG-thiol. The second embodiment (Type II) is shown in FIG. 3 (d) and consists of a thin (~20 nm) overcoat of $SiO_2$. A ~5 nm layer of Al or Cr is used to promote adhesion of the $SiO_2$. With this structure, the only exposed gold surface is the inside walls of the nanocavities, to which selective derivatization is performed.

Previous studies identified two fluorescence enhancement effects associated with nanocavity arrays—yield enhancement and surface plasmon excitation enhancement. These enhancements are studies in more detail using the two embodiments that allow for independent and direct measurement of enhancement factors—an embodiment with molecules located at the bottom (Type I) and an embodiment with molecules located on the sidewall (Type II). The enhancement factors—with additional denotation $M^{bottom}$ and $M^{side}$ for the Type I and II embodiments—are calculated based upon the respective surface areas—$A^{bottom}=\pi d2/4$ and $A^{side}=2\pi dh$—where d and h are the nanocavity diameter and height, respectively. When $h>d/2$, the surface area of the sidewall is greater than the surface area of the bottom. The enhancement factors associated with cavity-enhanced fluorescence in random arrays, which result in increased fluorescence yield given by $M^{bottom}_{cav}$ and $M^{side}_{cav}$, are determined. The surface plasmon excitation enhancement of fluorescence in periodic arrays given by $M^{bottom}_{SP}$ and $M^{side}_{SP}$ are also determined.

Individual detection zones, which are 75 µm×75 µm in size, are fabricated to characterize nanocavity enhancement and optimize surface plasmon excitation enhancement. These zones are arranged in a 3×3 array for the studies of molecular sensitivity in a real-time assay. E-beam lithography other suitable techniques may be used to fabricate individual detection zones. Another fabrication technique that may be used is nanoimprint lithography (S. Y. Chou, P. R. Krauss, and P. J. Renstrom, "Nanoimprint lithography," Journal of Vacuum Science & Technology B 14, 4129-4133 (2004)), in which arbitrary patterns can be written using e-beam or focused ion beam lithography on a master, then the master used to stamp out multiple copies (in an analogy to the process used for CD's and DVD's, which are basically a thin metal layer surrounded by dielectric layers).

3.1 Characterization of Nanocavity Enhancement

In order to characterize the enhancement in fluorescence yield produced by molecular confinement in a metallic nanocavity, and verify that the majority of the cavity enhancement results from an increase in fluorescence collection efficiency, detailed characterizations of derivatized nanocavities are undertaken.

Development and characterization of nanocavity derivatization procedures. Two different passivation procedures are employed for selective derivatization of the nanocavities, for which labeled avidin monolayers are formed. The passivation of the gold surfaces using mPEG-thiol follows the reference (K. L. Prime and G. M. Whitesides, "Adsorption of proteins onto surfaces containing end-attached oligo(ethylene oxide): a model system using self-assembled monolayers," Journal of the American Chemical Society 115, 10714-10721 (1993)) for the Type I embodiment, such that monolayer formation occurs only on the bottom of the nanocavities. A similar procedure is developed for the Type II embodiment (i.e., with the $SiO_2$ overcoat) to passivate the dielectric surfaces, thus allowing monolayer formation only on the exposed gold sidewalls. For Type II, dielectric surface passivation is performed using mPEG-silane. Introduction of the labeled avidin solution then allows monolayer formation on the exposed gold surfaces. An alternate method of selectively derivatizing the side-walls may also be employed, which follows a procedure developed with biotinylated thiol (D. M. Disley, D. C. Cullen, H. X. You, and C. R. Lowe, "Covalent coupling of immunoglobulin G to self assembled monolayers as a method for immobilizing the interfacial-recognition layer of a surface Plasmon resonance immunosensor," Biosensors and Bioelectronics 13, 1213-1225 (1998)), which binds strongly to gold surfaces. Cy-5 labeled neutravidin is then be used for the monolayer, where the neutravidin does not undergo a charge-charge interaction with the dielectric surfaces, but interacts strongly with the biotin layer via two of its biotin binding sites. This procedure is tested with two reference surfaces, a quartz surface which, after derivatization, should exhibit no measurable fluorescence, and a gold surface which should exhibit strong fluorescence. During the initial avidin labeling step, there is less than 1 Cy-5 molecule per labeled avidin, on average. This avoids any effects of energy transfer among a group of Cy-5 molecules clustered on a single avidin molecule, which would complicate the interpretation of cavity enhancement of fluorescence yield. The labeled avidin solution is then diluted using pure 1 µM avidin to the final concentration.

Previous studies suggest that the gold passivation procedure performed on a quartz reference surface results in a reduction in avidin surface concentration as compared to a quartz control surface without the passivation step. The reference samples are further characterized in terms of total fluorescence emission as well as ellipsometry studies to compare extinction at 280 nm (650 nm), which is directly proportional to the avidin (Cy-5) surface concentration. When the surface concentrations differ between reference and control, it is likely that the reference surface contains residual mPEG-thiol (on a quartz reference surface) or mPEG-silane (on a gold reference surface), which can be detected either with ellipsometry or XPS measurements. It may be that reduced surface concentration on the desired surface is an unavoidable consequence of the passivation process.

Because these passivation procedures require multiple steps involving mass transport into and out of nanoscale volumes, it is important that the final derivatized surfaces be fully characterized. One motivating factor behind the characterization studies is the determination of bound avidin surface concentration within the nanocavities, which cannot be performed using the standard XPS or ellipsometry techniques. Characterization is performed with two methods, initially using low aspect ratio $h/d\sim 0.1$ such that capillary effects play a negligible role in mass transport. After each successful characterization step, the aspect ratio is increased, with the goal of successfully derivatizing nanocavities with $h/d>1$.

The first characterization method employs radiolabeled avidin (with $^{125}$I) for the monolayer. The labeling procedure uses Enzymobeads (Bio-Rad Labs). Before labeling, sodium azide is removed from the avidin solution using Sephadex G-25 (Pharmacia) as sodium azide is a potent inhibitor of lactoperoxidase. The following reagents is added to an Enzymobead reaction vial: (1) 50 μL of 0.2 M phosphate buffer (pH 7.2); (2) 500 μL avidin solution; (3) 1 mCi Na$^{125}$I; (4) 25 μL of 2% glucose. This mixture is allowed to react for 40 min at room temperature. Unreacted Na$^{125}$I is removed by gel filtration (Sephadex G-25). Radiolabeling efficiency (RE) is determined by precipitating the labeled protein with 20% trichloroacetic acid (TCA) in presence of BSA as a carrier, and calculated using the following equation $$RE = (CPM_{solution} - CPM_{super})/CPM_{solution} \quad (1)$$

where $CPM_{solution}$ is the number of counts in 5 μL of the labeled protein solution before TCA precipitation and $CPM_{super}$ is the number of counts in 5 μL supernatant. Samples are counted using a Beckman Model 170M liquid scintillation counter. The specific activity of the iodinated protein is then calculated with the additional information of protein concentration determined from a UV-visible spectrophotometer at 278 nm. The radiolabeled avidin monolayer is formed using the same procedures as described previously. Radioassay is then used to determine the surface concentration of the immobilized avidin. Samples are counted for 1 min and the surface concentration calculated from $$\Gamma = (CPM/SA)/A_{surf} \quad (2)$$

where CPM is counts per minute, SA is the specific activity, and $A_{surf}$ is the effective surface area, which is just the total area of the nanocavities. The surface concentrations from nanocavity array samples are compared to reference samples that have undergone the same surface modification steps. The second characterization method involves using avidin labeled with metallic nanoparticles which are roughly 2 nm in size. Conjugation with metallic nanoparticles provides contrast under scanning electron microscope imaging, such that the location of the avidin monolayer and uniformity within the nanocavities can be directly determined and compared to the reference sample. Gold nanoparticle-avidin conjugates are available commercially. A high-resolution (~2 nm) field-emission SEM is employed for these measurements.

In situations where the surface concentration within the nanocavities is not as high as that for the reference samples (which may occur as h/d→1), the parameters of the derivatization procedures are adjusted. For example, one problem that may occur is that the wash step after passivation may not completely clear the volume of the nanocavities, which could cause interference with avidin monolayer formation. Possible ways to solve this would be to lengthen the duration of the wash step and/or perform the wash step at elevated temperature. Another issue that may arise is that of air bubbles becoming trapped within some of the nanocavities, preventing surface modification. If this occurs, the samples in buffer solution in a side-arm flask are degassed to promote wetting of the nanocavities before derivatization.

Study of reproducibility. A series of measurements are made to determine the reproducibility of the enhancement factor across multiple samples. Measurements are performed on 20 different samples of each embodiment (Type I and Type II), five periodic array samples and five random array samples fabricated using the etching procedure, and five of each pattern fabricated using the lift-off procedure. The nanocavity size is 150 nm diameter with 1 μm spacing, and the fluorescence outputs are measured relative to coated quartz substrates. The standard deviations from these measurements σref reflect variations in pattern fabrication, monolayer coating, and optical alignment and detection. When combined with the standard deviations of subsequent measurements described below (σmeas), it can be determined whether or not a change in a measured quantity such as the enhancement factor can be considered statistically significant. Using the nanofabrication process based upon metal etching, we obtained σref≤7% and 11% for d=200 nm for periodic and random arrays, respectively. The deviation is greater for d=150 nm, but with the new lift-off process, it is expected to reduce σref over the etching process for the same d. For subsequent studies, a nanofabrication process is chosen based upon the one that produces the smallest variation.

Fluorescence yield enhancement by a nanocavity. The following procedures are designed for determining the origin of the fluorescence yield enhancement by molecular confinement within a metallic nanocavity by using random arrangements of nanocavities where surface plasmon excitation enhancement is suppressed. The net increase in fluorescence yield is given by the factor $M_{cav} = M_{rad} \cdot M_{coll}$, where $M_{cav}$ is the fluorescence enhancement factor from the random arrays, $M_{rad}$ is due to an increase in the radiative rate, and $M_{coll}$ results from an increase in fluorescence collection efficiency. Previous studies using random nanocavity arrangements indicated that $M_{cav}$ ranged from about 10 for 120 nm diameter cavities to about 7 for 200 nm diameter cavities, with a predicted peak for 150 nm diameter. This observation suggests a strong influence of the nanocavity geometry on the emission properties of the fluors, most likely based upon the nanocavity aspect ratio h/d, where h is the height. This effect is studied experimentally by using nanocavity diameters ranging from 50-250 nm in diameter and comparing with results from simulation.

The total fluorescence enhancement factor due to the nanocavity is calculated for both Type I and Type II embodiments by measuring fluorescence output from random nanocavity arrangements relative to reference samples to give $M_{cav}$. These measurement rely on direct excitation of fluors within the nanocavities by incident light. Since the collection efficiency factor $M_{coll}$ is difficult to measure directly, it is instead indirectly determined from the measurements of $M_{cav}$ and $M_{rad}$. In order to estimate the fluorescence yield enhancement due to modification of the radiative rate, direct fluorescence lifetime measurements is performed with a time-correlated single photon counting system, where instead of imaging a single nanocavity at a time, a roughly 16 μm spot size is excited and imaged. This makes the experiments easier to perform and is one reason for using the random nanocavity arrays. With this method the lifetime can be measured for molecules on the bottom(Type I embodiment, giving $M^{bottom}_{rad}$) and on the side-walls (Type II embodiment, giving $M^{side}_{rad}$). For fluors on the sidewall, the fluor to metal separation is the thickness of one avidin molecule (approximately 5 nm), while for fluors on the bottom, the average separation is d/6>15 nm. Experiments with nanoparticles (A. Wokaun, H.-P. Lutz, A. P. King, U. P. Wild, and R. R. Ernst, "Energy transfer in surface enhanced luminescence," Journal of Chemical Physics 79, 509-514 (1983); J. Malicka, I. Gryczynski, Z. Gryczynski, and J. R. Lakowicz "Effects of fluorophore-to-silver distance on the emission of cyanine-dye-labeled oligonucleotides," Analytical Biochemistry 315, 57-66 (2003)) suggest maximum fluorescence enhancement due to increase in radiative rate for fluor to metal separation of about 9 nm. It is anticipated that the net cavity enhancement is maximized for aspect ratio h/d 100/150=0.67, due mainly to increase in collection efficiency. These measurements can identify the largest enhancement factor that can be obtained given practical limitations in nanofabrication and derivatization. For each embodiment, rigorous electromagnetic simulation (using FEMLAB, a commercial finite element method differential equation solver) of the radiative properties of a molecular dipole (using all polarization orientations) is performed at various positions within a metallic nanocavity in order to verify the experimentally derived $M_{coll}$. For example, for the Type II embodiment, dipoles are placed along the sidewall of the nanocavity, spaced 5 nm from the metal surface. The total radiative output from the nanocavity is compared to the output produced by the same dipole on a quartz surface to estimate $M_{coll}$. An average radiative enhancement is then be calculated based upon the $_{Mcoll}$ values produced for the three orthogonal dipole orientations, and dipole positions distributed along the bottom of the nanocavity (Type I) or along the sidewall (Type II).

The importance of these measurements is threefold: 1) to identify the spatial region of the nanocavity (i.e., Type I or Type II embodiment) where the greatest increase in yield due to cavity enhancement occurs, 2) to determine the contributions to net yield by radiative rate enhancement and collection efficiency enhancement, and 3) to determine the maximum net yield given the practical limitations in nanocavity aspect ratio, where h/d=0.67 is likely optimal with >10. The net cavity enhancement for a given fluor is independent of excitation intensity, and determines the photobleaching limited transduction sensitivity enhancement over detection performed on a quartz substrate, as done for end-point detection methods. This part of the study determines the nanocavity geometry (in terms of the values of diameter d and height h) that is applied for subsequent studies.

3.2 Optimization of Surface Plasmon Excitation Enhancement

The following procedures are designed to optimize the fluorescence excitation enhancement by surface plasmon coupling $M_{SP}$ in periodic arrays using Type I and Type II embodiments. Previous studies suggest that the surface-plasmon enhancement factor is nearly uniform for the two embodiments, i.e., $M^{bottom}_{SP} \sim M^{side}_{SP}$.

The total fluorescence enhancement factor $M_{tot}$ is calculated by the ratio of normalized fluorescence output from the periodic array to the reference surface, while the surface plasmon excitation enhancement factor $M_{SP}$ is given by the ratio of fluorescence between the periodic and random array of the same nanocavity diameter d and average spacing $\Lambda$. From these quantities, an apparent increase in fluorescence yield can be determined through the ratio $M_{cav}=M_{tot}/M_{SP}$, as described herein earlier.

Previous studies indicate that the intensity enhancement factor due to surface plasmon coupling MSP is about a factor of two, but it is expected that with optimization of the geometrical parameters, this factor may increase to 7 or more (H. J. Lezec and T. Thio, "Diffracted evanescent wave model for enhanced and suppressed optical transmission through sub-wavelength hole arrays," Optics Express 12, 3629-3651 (2004)). The origin of the excitation enhancement within the nanocavities results from the fact that under the condition of enhanced transmission (Y. Liu and S. Blair, "Fluorescence enhancement from an array of sub-wavelength metal apertures," Optics Letters 28, 507-509 (2003)) energy is concentrated within the nanocavities. The periodicity of the nanocavities not only supports coupling incident light from free space into surface plasmon modes, but also modifies the propagation properties of the surface plasmon (I. I. Smolyaninov, W. Atia, and C. C. Davis, "Near-field optical microscopy of two-dimensional photonic and plasmonics crystals," Physical Review B 59, 2454-2460 (1999)) through coherent scattering off the walls of the nanocavities, which results in constructive interference within the nanocavities. In these studies, the immobilized fluors act as local probes to the optical intensity buildup within the nanocavities. Surface roughness of the metallic nanocavity side-walls may manifest in the measurements of surface-plasmon excitation enhancement as the nanoscale roughness can serve as concentration points for light intensity buildup via the "lightning-rod" effect (A. V. Ermushev, B. V. Mchedlishvili, V. A. Oleinikov, and A. V. Petukhov, "Surface enhancement of local optical fields and the lightning-rod effect," Quantum Electronics 23, 435-440 (1993)). Any manifestation should average out across a nanocavity as the scale of the surface roughness is less than the size of the nanocavity. This effect can be quantified indirectly by estimating the surface roughness within the nanocavities for the Type I embodiment (the Type II embodiment should be similar) and incorporating these estimates into numerical models of light propagation through nanocavity arrays. Numerical modeling with FEMLAB can be used to aid in optimizing the nanocavity array geometrical factors for excitation enhancement and for characterizing the effects of sidewall roughness on the measured enhancement factors. Surface roughness is estimated experimentally by cross-section analysis of nanocavities that are strongly elliptical, such that the minor axis is in the 50-250 nm range, but the major axis is many μm's in length to make dicing and polishing more reliable. A high-resolution SEM can be used for cross-section inspection with a resolution of about 2 nm.

Excitation enhancement by surface plasmon coupling. The following procedures are designed to measure the fluorescence enhancement by fluors on the nanocavity sidewall $M^{side}_{SP}$ and by fluors at the bottom of the nanocavity $M^{bottom}_{SP}$ to determine the relative excitation efficiencies. For each embodiment, the fluorescence enhancement relative to the reference sample is determined for random and periodic arrays for different values of average nanocavity spacing $\Lambda$, ranging from about 600 nm to about 1 μm. These measurements are performed as a function of incidence angle, where the peak fluorescence corresponds to angles of peak transmission of the incident light owing to surface-plasmon coupling.

Incidence angle is changed only along the x-axis, so that the intersections of the coupling curves with the horizontal axis correspond to the angles of peak transmission (and peak fluorescence). These measurements result in a two-dimensional data set of $M_{SP}$ for each embodiment versus $\Lambda$ and incidence angle θ, from which values of peak fluorescence can be extracted. It can be predicted where maximal values may occur. In general, fluorescence enhancement should increase with decreasing $\Lambda$. In addition, there are discrete values of $\Lambda$ for which increased fluorescence enhancement should occur due to the overlapping of two or more coupling orders. For example, comparing the situations where $\Lambda$=1 μm and 678 nm, it is expected to obtain greater enhancement for $\Lambda$=678 nm at 27° than for $\Lambda$=1 μm at 25°. The reason for this is that at the smaller spacing, coupling at 27° corresponds (by design) to two overlapping diffraction orders, so that two surface plasmon waves are excited, thereby increasing the intensity within each nanocavity on average.

Optimization of surface plasmon enhancement using cross-coupling. The surface plasmon modes at each of the metal interfaces in general have different propagation constants, such that usually only one of these modes (the one at the metal-air interface) plays a role in enhanced transmission. However, the modes at the two interfaces can be coupled together (or cross-coupled (R. W. Gruhlke, W. R. Holland, and D. G. Hall, "Surface-plasmon cross coupling in molecular fluorescence near a corrugated thin metal film," Physical Review Letters 56, 2838-2841 (1986); R. W. Gruhlke, W. R. Holland, and D. G. Hall, "Optical emission from coupled surface plasmons," Optics Letters 12, 364-366 (1987))) when the momentum of the periodic lattice matches the differences in momenta of the two modes:

$$K = 2\pi/\Lambda = |k_{sp,1} - k_{sp,2}| \quad (3)$$

Under this condition, both interfaces play a role in enhanced transmission, and it is predicted that fluorescence excitation enhancement can be improved. For a given excitation wavelength (such as 633 nm), there is only one value of $\Lambda$ for which cross-coupling occurs, which is approximately 1150 nm for the first embodiment. However, as the difference in the refractive indices of the dielectrics at the two interfaces increases, the necessary value of $\Lambda$ decreases. For $\Lambda$=678 nm, the necessary refractive index on the substrate side is 1.513. Surface plasmon cross-coupling can be achieved by controlling the refractive index at the substrate by depositing a thin film of silicon oxynitride (SiON) between the gold and quartz substrate. With SiON deposited by plasma-enhanced chemical vapor deposition, one can have continuous control over refractive index in the range 1.46 to 2.05 by adjusting the relative ratio of oxygen and nitrogen atoms. Similar designs are tested for the second embodiment, where the effects of the finite thickness of $SiO_2$ on the top surface must be taken into account in the propagation constant of the surface plasmon wave at that interface.

The importance of these optimizations of excitation enhancement (in conjunction with the characterization of nanocavity enhancement) is twofold: 1) to determine the embodiment (Type I or Type II) that has the greatest overall fluorescence enhancement (i.e., $M_{tot} = M_{SP} \cdot M_{cav}$, where 60 or more is expected), and 2) to determine the geometrical and refractive index properties that maximize $M_{SP}$. The optimal embodiment and geometrical parameters are carried-forward to the studies of molecular sensitivity in real-time assays.

So far, these studies are directly comparable to the sensitivities obtained by end-point readout by scanning or imaging, where for the same incident power upon each hybridization zone, a hybridization zone comprising a nanocavity array offers enhanced fluorescence by a factor of $M_{tot} > 12$. This means that ~$1/M_{tot}$ fewer bound molecules per zone can be detected, implying that hybridization can be performed in roughly $1/M_{tot}$ the time. However, this is only part of the story as significant benefits can be gained by going towards a real-time detection approach that enables direct measurement of hybridization kinetics. These benefits include quantitative determination of target concentration in solution (which is very difficult with end-point analysis), discrimination against non-specific binding and heteroduplex formation, and short time to result. In order to perform real-time detection, there must be strong isolation from fluorescence produced by unbound species. As will be shown as follows, metallic nanocavity arrays provide greater isolation (by more than a factor of 10) than other surface-selective techniques, which, combined with the fluorescence enhancements already described, make this technique highly suited for DNA-based clinical diagnostics.

3.3 Determination of Molecular Sensitivity in Real-Time Assay

To determine molecular sensitivity in a real-time assay, real-time nucleic acid hybridization measurements are performed with a 3×3 array of hybridization zones, to verify that the metallic nanocavity arrays provide strong fluorescence isolation from unbound species in proportion to $1/\eta$ (which is an important consideration in any washless assay) and to determine assay time as a function of target concentration, even in situation where non-specific binding may be an issue. Validation studies relevant to clinical diagnostics are performed using multiple target species and controls. A second experimental setup is built using a low-noise cooled CCD camera in order to simultaneously image the 3×3 array. The nanocavity array embodiment (i.e., Type I or Type II) and geometrical parameters that produce the greatest fluorescence enhancements are used, as determined from studies described hereinbefore. The hybridization zones are spaced far enough apart from each other (about 1 mm) that manual spotting can be performed using a flexible Micromachined gasket with open wells to isolate one zone from another. The T3 polymerase promotor site is used as a model system; T3 5'-(AATTAACCCTCACTAAAGGG)-3' and complementary anti-T3 are commercially available, and can be fluorescently labeled with Cy-5. A synthetic 60-mers is also employed in the validation studies. Sample solution containing fluorescently labeled target and non-target species is introduced to the surface using a flow cell (Y. Liu, J. Bishop, L. Williams, S. Blair, and J. N. Herron, "Biosensing based upon molecular confinement in metallic nanocavity arrays," Nanotechnology 15, 1368-1374 (2004)) (see FIG. 4), which resides on the top surface of the nanocavity samples.

Nanocavity derivatization with anti-T3 probe. The following procedures are designed to characterize the immobilization of capture oligonucleotides (anti-T3 for these studies) within the nanocavities. Formation of the avidin monolayer is followed by a solution of 0.15 µM 5'-biotinylated anti-T3 which self-assembles on top of the avidin-coated surface (J. N. Herron, S. zumBrunnen, J.-X. Wang, X.-L. Gao, H.-K. Wang, A. H. Terry, and D. A. Christensen, "Planar waveguide biosensors for nucleic acid hybridization reactions," Proceedings SPIE 3913, 177-184 (2000)). Derivatization procedures are characterized using radio-labeled anti-T3 to determine probe surface concentration and optimize the procedure. For reproducibility purposes, these procedures are implemented identically in all 9 zones of the 3×3 array.

Radiolabeled oligonucleotides are prepared by end labeling with ($^{32}$P)phosphate. For determining the surface concentration of immobilized capture oligo (i.e., anti-T3), 5'-biotinylated oligos are labeled with ($\alpha$-$^{32}$P)ATP using terminal transferase. This enzyme adds ($^{32}$P)AMP to the 3' end of the oligo. A commercial 3' end labeling kit (Perkin Elmer) is used to perform the reaction. The extra adenosine group is not expected to interfere with binding of the labeled oligo to the immobilized avidin monolayer. Radiolabeling efficiency is determined using a similar procedure as described before with equation (1). The oligo concentration is determined using a UV-vis spectrophotometer at 260 nm. After self-assembly of the radiolabeled anti-T3 onto the avidin monolayer, the probe surface concentration is determined according to equation (2) using the radioisotope detector. The surface concentration within the nanocavity array is compared to that obtained for a planar reference sample. The derivatization procedure for the nanocavities may need to be adjusted as a result of this comparison; for example, if the nanocavity surface concentration is lower, then it is necessary to increase the concentration of anti-T3 in solution from 0.15 µM before the self-assembly step. Before the real-time hybridization experiments are performed, a calibration between bound surface concentration and fluorescence intensity is performed. Using radiolabeling one can know the bound probe concentration. One can then perform the same surface modification procedures with Cy-5 3' end-labeled anti-T3 (with labeling ratio determined by UV-vis absorption) to allow direct relation between measured fluorescence intensity and bound concentration. This relationship can be used in conjunction with the two-compartment model to determine the detection limits in terms of the number of bound target molecules and to optimize the probe concentration.

Determination of signal to background ratio. The following procedures are designed to verify fluorescence isolation from unbound species and to determine the detection sensitivity taking into account non-specific binding. Because detectable fluorescence can only be produced from within a nanocavity, random variation in fluorescence from non-target molecules only occurs when those molecules randomly diffuse into and out of the nanocavity (although some fraction may produce a signal due to non-specific binding). The nanocavity surface area represents a fraction $\eta$ of the total zone area ($\eta \sim 2\text{-}10\%$), so that the background signal from unbound species should be less by a factor of approximately $1/\eta$ ($\sim$10-50) than in other washless, surface selective fluorescence sensors such as a planar waveguide or fluorescence-SPR where the sensing surface represents 100% of the zone area. Again, these studies are performed with the 3×3 array where all zones are derivatized with anti-T3 probe.

Figure 5:
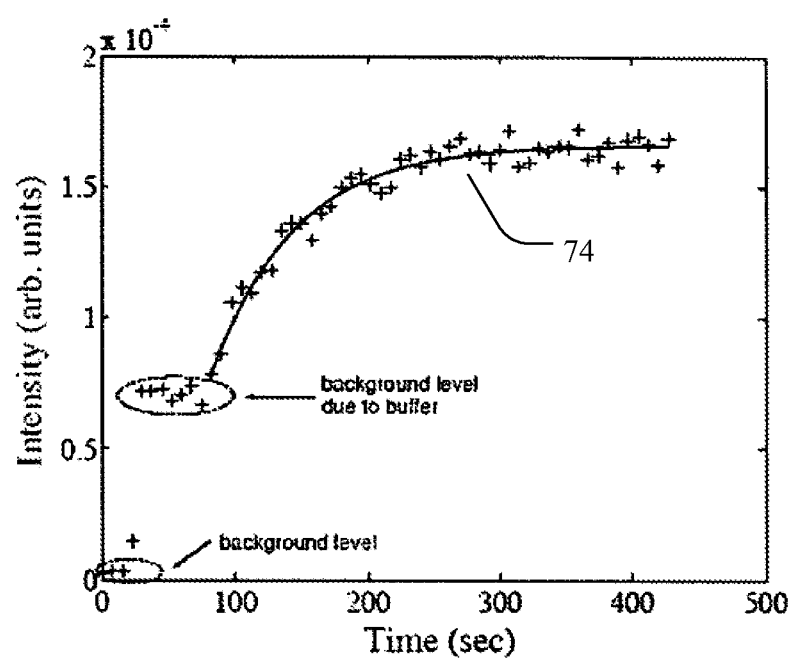
FIG. 5 is a graph (74) that illustrates real-time hybridization between T3 in solution and anti-T3 immobilized within the nanocavities.

Because the transduction area in the nanocavity architectures is so small, diffusion of the target molecules into the sensing regions is slightly slower than if the transduction area were 100% of the sensing area. The first step is then to study hybridization kinetics of the labeled target as a function of target concentration in solution, as compared to a planar waveguide. Target oligos (T3), labeled at the 5' end with Cy-5 dye are prepared in solution with a concentration $C_n$, where n is the trial number. Typical Molar concentrations range from $10^{-8}$ to $10^{-12}$. When introduced into the flow cell, T3 hybridizes to probe oligos on the capture monolayer and form duplex DNA. The hybridization kinetic curve 74 is measured for each $C_n$ through the time dependence of the fluorescence excited by light intensity within each nanocavity (as shown in FIG. 5). By comparing the kinetic curves between the two nanocavity architectures and the waveguide, with greatly different fill fractions, the increase in diffusion time can be estimated via the parameter $k_M$, as defined subsequently. In addition, optimization of immobilized probe concentration is performed by maximizing binding rate.

Figure 6:
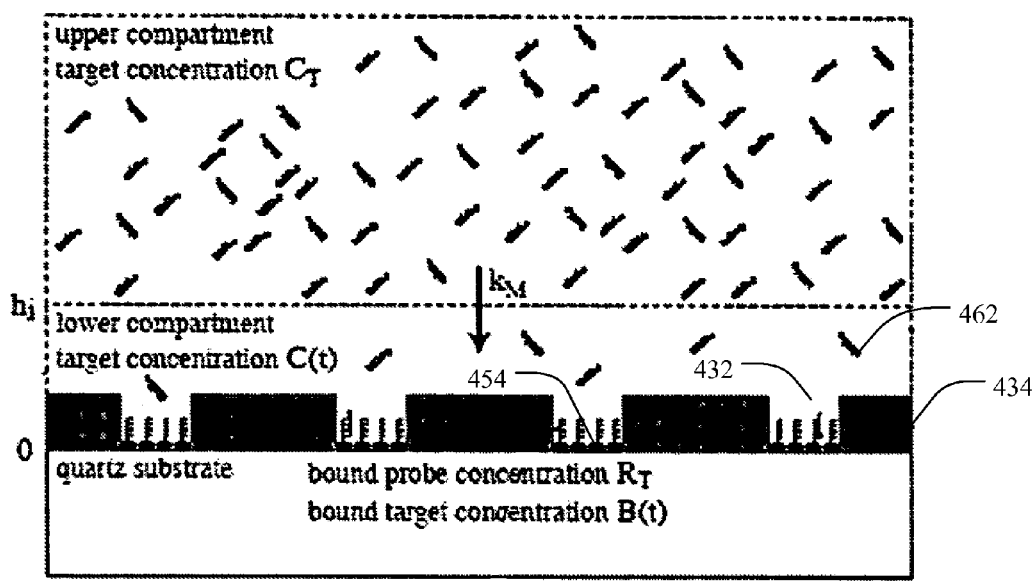
FIG. 6 schematically depicts the geometry associated with a two compartment model that simulates binding between capture molecules and target molecules (432, 434, 454, 462).

One can analyze the kinetic curve using the two-compartment model (D. G. Myszka, X. He, M. Dembo, T. A. Morton, and B. Goldstein, "Extending the range of rate constants available from BIACORE: interpreting mass transport-influenced binding data," Biophysical Journal 75,583-594 (1998)):

$$dC(t)/dt = 1/h_i\{-k_\alpha C(t)(R_T-B(t))+k_d B(t)+k_M(C_T-C_T-C(t))\} \quad (4)$$

$$dB(t)/dt = k_\alpha C(t)(R_T-B(t))-k_d B(t) \quad (5)$$

where $h_i$ is the height of the lower compartment where significant target depletion can occur, $k_\alpha$ is the association rate, $k_d$ is the dissociation rate (which typically can be ignored for specific binding at room temperature), $k_M$ accounts for mass transport between the upper and lower compartments, $C(t)$ is the target concentration in the lower compartment, $R_T$ is the probe concentration, and $C_T$ is the target concentration in the upper compartment (which is assumed constant due to injection from the flow cell). These parameters are illustrated in FIG. 6 showing nanocavities 432 having capture molecules 454 for identifying species 462. The purpose for using the two-compartment model is that, through the fitting constant $k_M$, the effect of mass transport to the sparse array of detection sites can be determined and compared to a planar waveguide sensing modality in which the fill fraction is 100%. In order to differentiate the effects of non-specific binding, the two-compartment model is modified to describe the binding of two species to the surface with association constants $k_{\alpha 1}$ and $k_{\alpha 2}$. In this case, two bound concentrations $B_1(t)$ and $B_2(t)$ are obtained, and the density of available binding sites is given by $R_T-B_1(t)-B_2(t)$. One may also have to incorporate the effects of dissociation for the non-specific species. The ultimate goal for clinical diagnostics is to use the two-compartment model to analyze the kinetic curve at each hybridization zone to obtain the unknown concentration $C_T$ of the desired target in solution.

Figure 7:
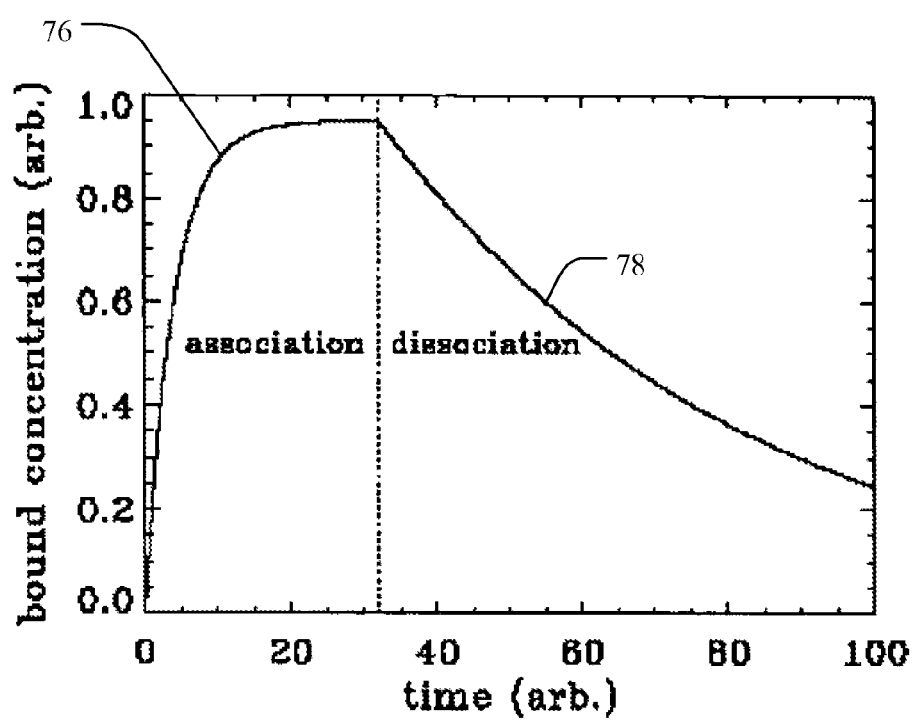
FIG. 7 is a model association/dissociation curve (76, 78).

The next step is to perform kinetic measurements using a second labeled sequence of the same length as T3/anti-T3 to determine the kinetic coefficients in the two-compartment model for non-specific binding (NSB). The sequences of these "background" oligos are chosen so as not to specifically bind to either the target or probe molecules. These background oligos diffuse into the nanocavities and produce a random background signal, which could mask the kinetic curve produced by bound species, and may also non-specifically bind, which produces a signal that mimicks the kinetics of the target species (but with a different rate and equilibrium value (H. Dai, M. Meyer, S. Stepaniants, M. Ziman, and R. Stooughton, "Use of hybridization kinetics for differentiating specific from non-specific binding to oligonucleotide microarrays," Nucleic Acids Research 30, (2002))). NSB can occur under certain experimental conditions (e.g., low ionic strength) between non-target species and immobilized avidin which has a net positive charge at neutral pH. These measurements are made as a function of $C_n$, where larger concentrations in the range $10^{-6}$ to $10^{-10}$ are used. Here, both association (i.e., binding) and dissociation curves 76 and 78, respectively, are obtained, as illustrated in FIG. 7. The dissociation curve 78 is generated by flowing buffer solution through the flow cell, and allows determination of $k_d$ for non-specific binding. From the determination of the kinetic coefficients ($k_\alpha$ and $k_d$ which should be relatively constant across concentration of non-specific species), one can then use the modified dual-rate two-compartment model to differentiate between specific and non-specific binding, where the fitting parameters in the model is $C_1$ (initial target concentration) and $C_2$ (initial concentration of species that non-specifically bind). Herron et al. (J. N. Herron, S. zumBrunnen, J.-X. Wang, X.-L. Gao, H.-K. Wang, A. H. Terry, and D. A. Christensen, "Planar waveguide biosensors for nucleic acid hybridization reactions," Proceedings SPIE 3913, 177-184 (2000)) showed that NSB can be virtually eliminated by using a neutravidin monolayer instead of avidin. If it determines that NSB is occurring to the point that NSB kinetics cannot be discriminated from the target kinetics, then one should modify the derivatization procedure to employ neutravidin on silanized surfaces according to Herron et al. (for the Type I embodiment) or biotinylated thiol (D. M. Disley, D. C. Cullen, H. X. You, and C. R. Lowe, "Covalent coupling of immunoglobulin G to self assembled monolayers as a method for immobilizing the interfacial-recognition layer of a surface Plasmon resonance immunosensor," Biosensors and Bioelectronics 13, 1213-1225 (1998)) (for the Type II embodiment), followed by characterization procedures as described previously.

Measurements are then performed using both the target and background species. The background oligos diffuse into the nanocavities and produce a random background signal. Three sets of measurements are made to determine the detection sensitivity. The first set is as a function of target concentration $C_n$, where the concentration of non-specific oligos is also $C_n$. This situation simulates the conditions for a two-zone sensor array. The second set has target concentration $C_n$, but non-specific concentration 10 $C_n$, thus simulating a 10-zone array. The final set has non-specific concentration of 100 $C_n$. From the two-compartment model, one can then determine the minimum detectable target concentration and the associated number of bound target molecules. It is anticipated that the detection limit is a factor of $M_{tot}/\eta$ lower for the nanocavity architectures than the waveguide (taking into account the normalization between surface intensity of the evanescent field of the waveguide and the intensity of direct excitation on the quartz reference surface from which $M_{tot}$ was derived, where this normalization factor will be of order 1). These measurements should demonstrate that the nanocavity array has improved background isolation as compared to the planar waveguide (as evidenced by greater ratio between the hybridization signal and background noise). In addition, these studies allow the determination of the hybridization time required to obtain quantitative determination of target concentration, as a function of that target concentration (i.e., lower $C_T$ will require longer hybridization times). Because of the background isolation and increased detection sensitivity, it is expected that the necessary hybridization time is at least a factor $1/\eta$ shorter with the nanocavity array zones as compared to the waveguide zones.

Figure 8:
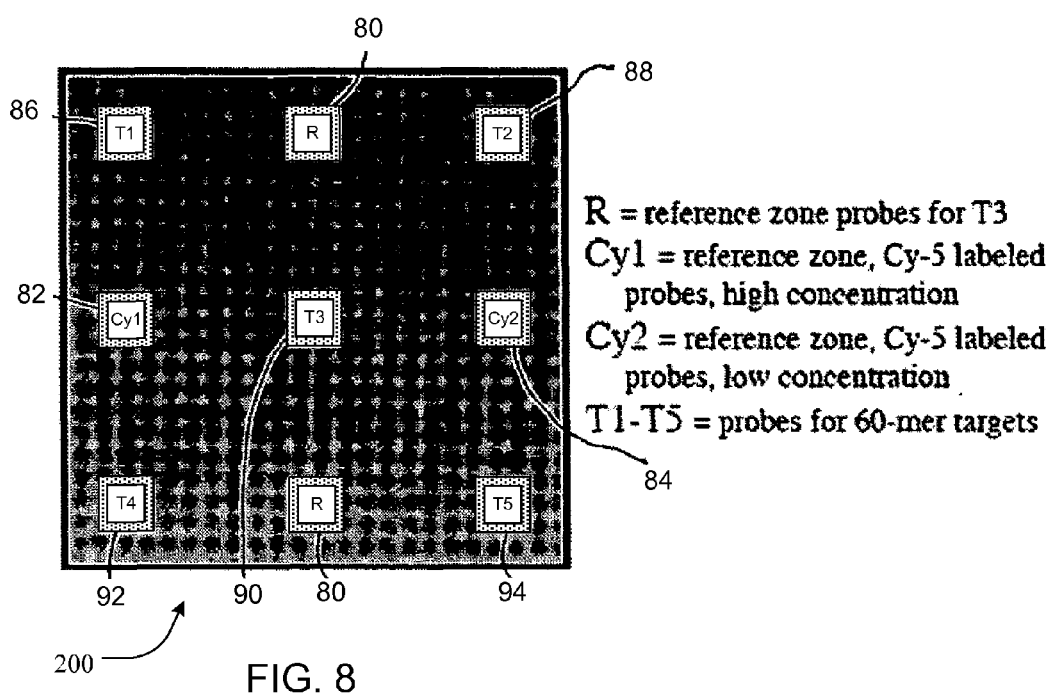
FIG. 8 illustrates the patterning of individual detection zones of a 3 x hybridization array for validation studies (80, 82, 84, 86, 88, 90, 92, 94, 200).

Validation studies. To validate the array system, the 3×3 array 200 (as shown in FIG. 8) is used to screen across multiple synthetic targets (five different 60-mer sequences with varying degrees of overlap, with two sequences differing by only a single base) using five hybridization zones 86, 88, 90, 92 and 94 that are derivatized with complementary probes and the remaining four zones, 80, 80, 82, and 84. The detection zones are placed far enough apart to enable mutual isolation of the detection zones during immobilization of probe molecules. The purpose of using 60-mers is that they are more representative of the sequence length of PCR products in clinical diagnostics setting. Because of the increased oligo length, the hybridization kinetics is slower than in the previous studies due to reduced diffusion. Two of four reference zones are derivatized with Cy-5 labeled probes at different concentrations (to be used as fluorescence intensity references) and the remaining two with anti-T3 (where Cy-5 labeled T3 are introduced in high concentrations in all experiments as a model source of background and NSB), as illustrated in FIG. 8.

In these studies, the five target species in varying concentrations (roughly 10 pM to 1 nM) with T3 at 100 nM concentration are introduced as background. The goal is to study discrimination across the five targets (in terms of obtaining CT for each) in a complex environment where hybridization kinetics varies strongly across hybridization zones due to differing target concentration and where heteroduplex formation occurs. Again, in addition to the quantitative determination of target concentrations, important outcomes are the hybridization time required to make that determination and comparison with a planar waveguide.

These studies determine the ultimate performance of metallic nanocavity arrays as detection zones of a real-time hybridization array. Validation of this platform in situations relevant to clinical diagnostics, in particular, to infectious disease where assay time is critical, is performed. It is anticipated quantitative determination of target concentrations can be made with hybridization kinetics in less than 30 minutes, even in complex environments where the effects of non-specific binding and heteroduplex formation are important. It should also be noted that further refinement of the techniques may be possible by using electric-field enhanced hybridization (R. J. Heaton, A. W. Peterson, and R. M. Georgiadis, "Electrostatic surface plasmon resonance: direct electric field-induced hybridization and denaturation in monolayer nucleic acid films and label-free discrimination of base mismatches," Proceedings of the National Academy of Sciences 98, 3701-3704 (2001); H.-J. Su, S. Surrey, S. E. McKenzie, P. Fortina, and D. J. Graves, "Kinteics of heterogeneous hybridization on indium tin oxide surfaces with and without an applied potential," Electrophoresis 23, 1551-1557 (2002)) where it has been shown that hybridization kinetics can be increased (through drift-induced oligo transport to the surface, such that $k_M$ in the two-compartment model would increase in value) in addition to improving binding specificity through field reversal. The gold metallic layer upon which the nanocavity array sensing zones are fabricated would lend itself naturally to such a technique.

4. Quantitative Study and Comparison of Enhanced Molecular Fluorescence by Periodic Metallic Nanostructure Architectures The following study is designed to quantitatively compare fluorescence enhancement mechanism and detection sensitivities in complex environments for three periodic metallic nanostructure architectures for real-time hybridization arrays. Each nanostructure arrangement is conducive to real-time measurement of hybridization kinetics, is scalable to a large array format, and may possess sufficient molecular sensitivity to bypass the need for molecular amplification steps required by other methodologies.

4.1 Fabrication of Metallic Nanostructure Arrays

To develop nanofabrication methods that are both expedient and repeatable, fabrication of metallic nanostructure arrays are based upon the technique of lift-off, which bypasses the need for a hard mask and metal dry-etching. Dry etching of metals requires very tight process control to produce repeatable results. Lift-off therefore results in significantly increased device yield.

Even though expensive from a manufacturing standpoint, e-beam lithography is the most stable, cost-effective, and flexible nanolithography tool available in an academic environment. Other techniques to fabricate metallic nanostructure arrays include interference lithography (S. C. Lee and S. R. Brueck, "Nanoscale two-dimensional patterning on Si(001) by large-area interferometric lithography and anisotropic wet etching," Journal of Vacuum Science & Technology B 22, 1949-1952 (2004)), which exposes patterns in photoresist based upon the interference of two or more optical plane waves; nanosphere lithography (W. A. Murray, S. Astilean, and W. L. Barnes, "Transition from localized surface plasmon resonance to extended surface plasmon-polariton as metallic nanoparticles merge to form a periodic hole array," Physical Review B 69, 165407 (2004)), in which a self-assembled monolayer of small dielectric spheres is used as a mask for deposition/etching steps; and nanoimprint lithography (S. Y. Chou, P. R. Krauss, and P. J. Renstrom "Nanoimprint lithography," Journal of Vacuum Science & Technology B 14, 4129-4133 (2004)), in which arbitrary patterns can be written using e-beam or focused ion beam lithography on a master, then the master used to stamp out multiple copies (in an analogy to the process used for CD's and DVD's, which are basically a thin metal layer surrounded by dielectric layers).

Three array architecture, including Nanocavity array architecture, Bullseye architecture, Nanoparticle array architecture, are fabricated. For each architecture, individual detection zones which are 75 μm×75 μm in size are fabricated.

Figure 9:
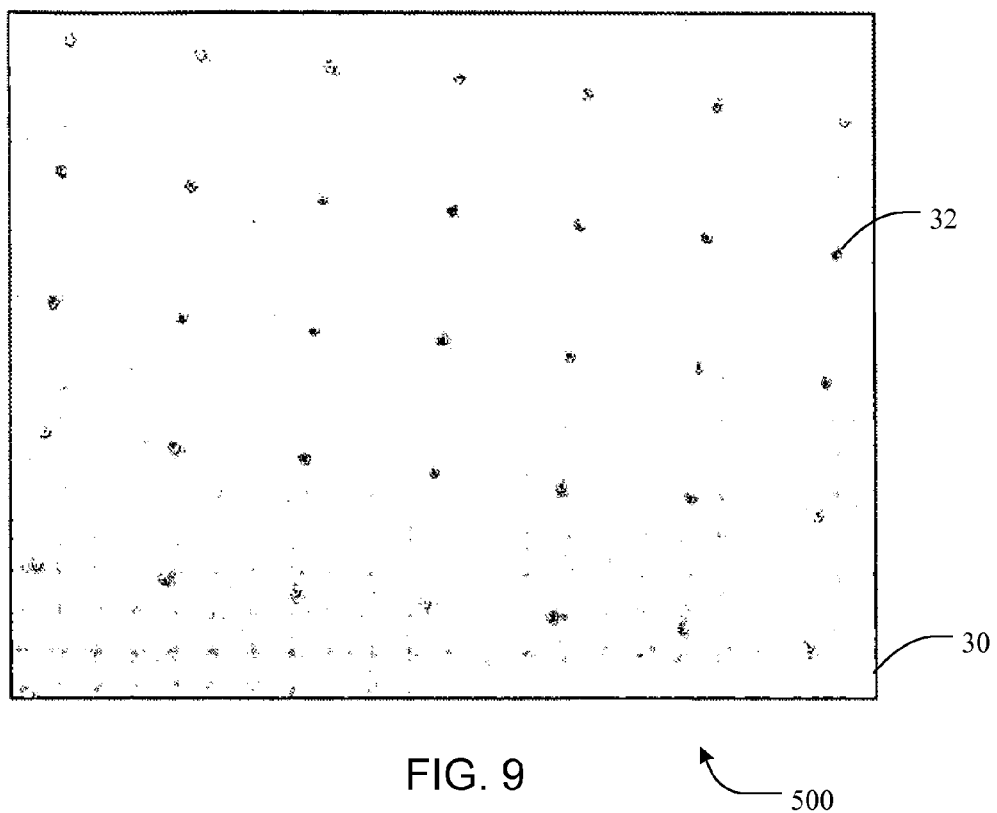
FIG. 9 is a scanning electron microscopy (SEM, 500) image of a square lattice periodic nanoaperture array (30, 32).

Nanocavity array architecture. Nanocavity arrays are produced in 60 nm thick gold films using electron beam lithography followed by a reactive ion etching (RIE) step. The gold layer is deposited on clean quartz substrates by RF-magnetron sputtering followed by a 300 nm silicon-nitride film deposited by plasma enhanced chemical vapor deposition (PECVD). Then a layer of PMMA is spun on for 45 seconds at 4000 rpm and baked to remove the solvent. An identical second coating is applied with an additional baking step thereafter to produce a PMMA layer of total thickness 350 nm. The nanocavity array patterns are drawn on this positive resist using e-beam and the exposed PMMA developed in a solution of MIBK:IPA 1:3 for 70 seconds. The pattern from PMMA is transferred to silicon-nitride using RIE with etching gases of $CF_4$ and $O_2$, then continue to transfer the pattern to gold with etching gases $Cl_2$ and $Ar_2$. FIG. 9 shows an SEM image 500 of one nanocavity array 30. The array 30 has $\Lambda=1$ μm and d=150 nm. In addition, a ~20 nm layer of SiON (preceded by a thin adhesion layer) is deposited on top of the ~100 nm gold layer before lift-off. After lift-off, the only exposed gold surfaces are the interior walls of the nanocavities. This modified structure has two advantages. First, because the top and bottom metal interfaces are more nearly symmetric in terms of the effective propagation constants of the SPP modes at each interface 3, there is stronger coupling between these SPP modes, resulting in greater light transmission (L. Martin-Moreno, F. J. Garcia-Vidal, H. J. Lezec, K. M. Pellerin, T. Thio, J. B. Pendry, and T. W. Ebbesen, "Theory of extraordinary optical transmission through subwavelength hole arrays," Physical Review Letters 86, 1114-1117 (2001)) and therefore, greater intensity enhancement within the nanocavities. In this symmetric situation, the maximum intensity enhancement is estimated to be a factor of 7 (H. J. Lezec and T. Thio, "Diffracted evanescent wave model for enhanced and suppressed optical transmission through subwavelength hole arrays," Optics Express 12, 3629-3651 (2004)) The second advantage is that the same surface modification chemistry can be shared between the nanocavity and nanoparticle architectures, where selective derivatization of the exposed gold surfaces is performed.

It is well-known (H. J. Lezec and T. Thio, "Diffracted evanescent wave model for enhanced and suppressed optical transmission through subwavelength hole arrays," Optics Express 12, 3629-3651 (2004)) that the transmission enhancement is maximum for nanocavity spacings $\Lambda$ slightly less than the excitation wavelength $\lambda$, and for nanocavity diameters d~$\lambda$/3. However, because of nanocavity effects, this may not be optimal for fluorescence emission. Therefore, nanocavity diameters ranging from 100 to 250 nm are fabricated. This optimal spacing is designed for normally incident light. In order to minimize transmitted excitation light from producing background signal at the detector (i.e., leakage through the spectral filter), spacings in the 750-850 nm range are used, as this allows collection of fluorescence emission normal to the surface over a ±10° cone half-angle without the collection of transmitted excitation light, which exits at 12-17°. After sample fabrication, linear transmission measurements versus wavelength at normal incidence and versus angle of incidence at a fixed wavelength (633 nm) are performed. These measurements allow for parameter optimizations to maximize transmission and to determine sample-to-sample repeatability.

Bullseye architecture. Nanofabrication of this architecture is quite a bit more involved than the nanocavity sub-arrays. A new process for fabricating this architecture can be based upon e-beam lithography. This process requires accurate alignment (better than about 60 nm) of one e-beam lithography step to another. The first step is to place alignment marks on the substrate using optical lithography. These alignment marks are made using small gold crosses and are oriented at the corners of an 80 μm by 80 μm square, which is approximately the field of view of the e-beam system. The next step is to pattern the 3×3 sub-array of circular corrugations into the quartz substrate with S=25 μm center-to-center spacing. This process occurs via e-beam lithography with positive resist. Before exposure, the e-beam is switched to imaging mode to locate the calibration marks. Once located, a grid can be created on the controlling computer with the alignment marks at the corners. The bullseye sub-array pattern is then exposed using coordinates on this grid with a periodicity 580 nm, which is nearly optimal for an excitation wavelength of 633 nm (T. Thio, K. M. Pellerin, R. A. Linke, H. J. Lezec, and T. W. Ebbeson, "Enhanced light transmission through a single subwavelength aperture," Optic Letters 26, 1972-1974 (2001)). About 10 annular rings are sufficient to achieve the maximum enhancement. After exposure and development, the quartz substrate is dry etched to a depth of about 40-50 nm, which again is nearly optimal (too deep of an etch renders these annular regions of the gold nearly transparent). From here, the process follows the procedure of fabricating the nanocavity arrays, with the exception of the additional alignment step needed during e-beam lithography to place a nanocavity in the center of each circular corrugation. Lift-off leaves a nanocavity in the center of the bullseye, while the corrugation is automatically produced (or cloned) onto the metal by deposition onto the corrugated substrate. After fabrication, these samples are imaged with SEM to determine the placement of the nanocavity with respect to the center of the bullseye corrugation. Then, linear transmission spectra are taken to determine the transmission enhancement factor and the effect of placement accuracy on the enhancement. Since the effective wavelength of the top-surface SPP mode is roughly $\lambda$=633 nm, about 0.1$\lambda$ accuracy is required. The placement accuracy is verified using rigorous electromagnetic simulation in FEMLAB. After the determination of necessary alignment accuracy, bullseye nanocavity patterns that have acceptable placement are used in specific applications. In the event that the device yield is too low (i.e., less than 25%), the nanocavities of this structure can be milled precisely using dbFIB.

Figure 10:
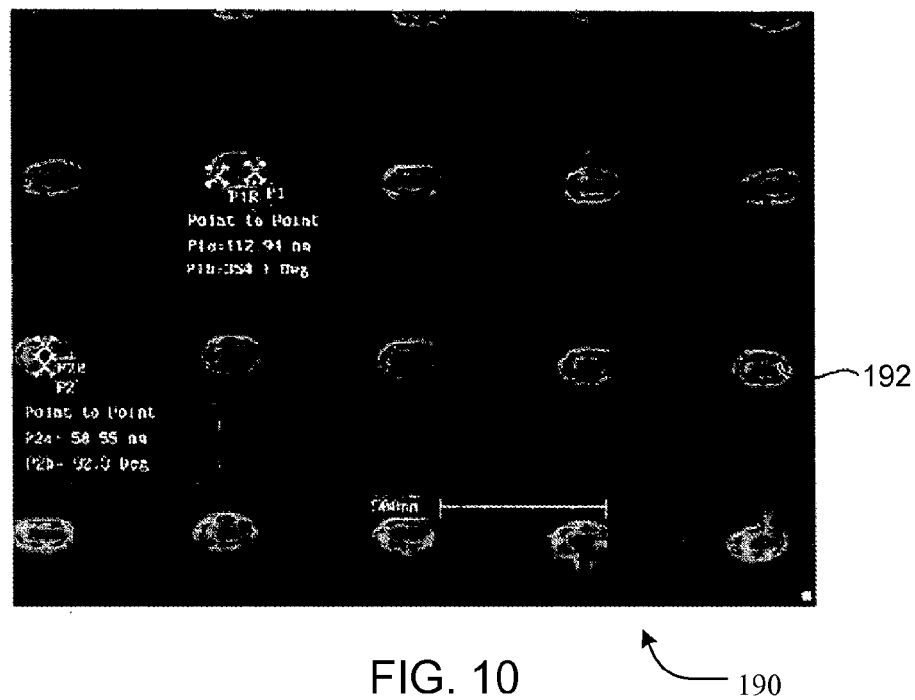
FIG. 10 is an SEM image of a metallic nano particle array fabricated through e-beam lithography with a lift-off process (190).

Nanoparticle array architecture. This architecture is the most straightforward to fabricate. A positive e-beam resist (PMMA for example) is spun onto the quartz substrate and baked. The resist is then exposed with the desired nanoparticle array pattern. Developing removes the exposed areas. After deposition of the chromium adhesion and gold layers, the resist is removed during a lift-off process, leaving behind the metallic nanoparticle array. An example nanoparticle array pattern 190 is shown in FIG. 10. The pattern 190 includes particles 192, where the particles are elliptical in shape with 113 nm major axis and 60 nm minor axis, and the thickness is 30 nm.

As opposed to the nanocavity architectures, optical testing is performed on nanoparticle arrays in reflection mode as coupling into the local surface plasmon modes of the nanoparticles occurs via total internal reflection (TIR) from a prism, as illustrated in FIG. 1. The nanoparticles are arranged in a periodic square lattice with $\Lambda$~150-250 nm, which prevents any particle-particle interaction that would shift and dampen the individual nanoparticle resonance (W. A. Murray, S. Astilean, and W. L. Barnes, "Transition from localized surface plasmon resonance to extended surface plasmon-polariton as metallic nanoparticles merge to form a periodic hole array," Physical Review B 69, 165407 (2004)), while at the same time eliminates any diffraction orders from the incident excitation light as $\Lambda<\lambda$/2. In reflection, the localized surface plasmon resonance of each nanoparticle is indicated by dips (as opposed to peaks in transmission for the nanocavities). Nanoparticle shapes and thicknesses are designed to maximize absorption at 633 nm under TIR illumination, roughly elliptical with 110 nm major axis and 100 nm minor axis and 30 nm thickness.

Improving geometry control. One of the issues that arises during long exposures in electron beam lithography is the stability of the writing beam. Thermal drift of the electron beam may result in slight variation in the positions of nanocavities in an array. This problem worsens with increasing pattern complexity. The effect of nonuniform spacing of nanocavities (i.e., inhomogeneous broadening), for example, is a reduction of the excitation efficiency of surface plasmons, thereby reducing the achievable intensity enhancement factor within the nanocavities. Geometry nonuniformity can be significantly reduced when using "faster" e-beam resists. Fast resists require reduced exposure dosage, and hence the same pattern can be written in less time, but these resists do tend to have reduced resolution. Many different positive and negative resists can be investigated to find a faster resist that retains enough resolution for the patterns.

4.2 Selective Derivatization of Nanostructures

The following studies are designed are to develop and characterize selective surface modification procedures for the nanostructure architectures.

Surface modification for measurement of fluorescent enhancement. A passivation procedure for the metal surface has been developed so that the fluorescing monolayer only covers the bottom, quartz, surface of the nanocavities. The passivation procedure follows Prime et al. (K. L. Prime and G. M. Whitesides, "Adsorption of proteins onto surfaces containing end-attached oligo(ethylene oxide): a model system using self-assembled monolayers," Journal of the American Chemical Society 115, 10714-10721 (1993)): dissolve mPEG-thiol (in powdered form) to a concentration of 1 µmol/L in ethanol; apply solution to gold surfaces for 24 hours in a $N_2$ filled glove box at room temperature and atmospheric pressure, then rinse in ethanol and dry in $N_2$; apply labeled avidin solution to form the monolayer. Reference surfaces for this procedure consisted of a smooth gold surface, which after passivation and monolayer coating, did not produce a measurable fluorescence signal in a fluorescence microscope, and a quartz substrate, which after passivation and monolayer coating, produced a fluorescence signal roughly 85% of a coated quartz surface without passivation, which is likely the result of a slight reduction of bound surface concentration.

A similar procedure can be developed for the nanostructure array architectures, where the dielectric surfaces are passivated, thus allowing monolayer formation only on the exposed gold sidewalls of the nanocavities or gold surfaces of the nanoparticles. Dielectric surface passivation is performed using mPEG-silane. Introduction of Cy-5 labeled avidin solution then allows monolayer formation on the exposed gold surfaces. Alternatively, selectively derivatizing the side-walls may also be employed, which follows a procedure developed with biotinylated thiol (D. M. Disley, D. C. Cullen, H. X. You, and C. R. Lowe, "Covalent coupling of immunoglobulin G to self-assembled monolayers as a method for immobilizing the interfacial-recognition layer of a surface plasmon resonance immunosensor," Biosensors and Bioelectronics 13, 1213-1225 (1998)), which binds strongly to gold surfaces. Cy-5 labeled neutravidin is then be used for the monolayer, where the neutravidin does not undergo a charge-charge interaction with the dielectric surfaces, but interacts strongly with the biotin layer via two of its biotin binding sites. A third alternative is to passivate with mPEG-silane and derivatize the exposed gold surfaces with thiol-conjugated oligos (J. Malicka, I. Gryczynski, and J. R. Lakowicz, "DNA hybridization assays using metal-enhanced fluorescence," Biochemical and Biophysical Research Communications 306, 213-218 (2003)). These procedures are tested with two reference surfaces, a quartz surface which, after derivatization, should exhibit no measurable fluorescence, and a gold surface which should exhibit strong fluorescence, as measured with a scanning confocal fluorescence microscope.

The new procedures are tested first on the nanoparticle array architecture, as direct imaging by the fluorescence microscope in reflection mode can be used to determine selective derivatization of the nanoparticles with Cy-5/avidin. The other two nanocavity array architectures can be tested next. By using reflection mode, the absence of fluorescence from the top surface can be verified; fluorescence from within the nanocavities can be detected. As further verification, transmission mode can be used to verify that the only detectable fluorescence comes from the nanocavities.

Because these surface modification procedures require multiple steps involving mass transport into and out of nanoscale volumes, it is important that the final derivatized surfaces be fully characterized. One motivating factor behind the characterization studies is the determination of bound avidin surface concentration within the nanocavities or upon the nanoparticles. The characterization methods are described herein in Example 4.

Surface modification for nucleic acid hybridization. The T3 polymerase promotor site is used as a model system for nucleic acid hybridization to determine background isolation and molecular sensitivity across the three architectures. T3 5'-(AATTAACCCTCACTAAAGGG)-3' and complementary anti-T3 are commercially available, and can be fluorescently labeled with Cy-5. Capture oligonucleotides (anti-T3 for these studies) are immobilized onto the nanostructures. Formation of the avidin monolayer is followed by a solution of 0.1-10.0 µM 5'-biotinylated anti-T3 which self-assembles on top of the avidin-coated surface (J. N. Herron, S. zumBrunnen, J.-X. Wang, X.-L. Gao, H.-K. Wang, A. H. Terry, and D. A. Christensen, "Planar waveguide biosensors for nucleic acid hybridization reactions," Proceedings SPIE 3913, 177-184 (2000)). Radiolabeled oligonucleotides (anti-T3 for this part of the study) are prepared by end labeling with ($^{32}$P) phosphate. For determining the surface concentration of immobilized capture oligo (i.e., anti-T3), 5'-biotinylated oligos are labeled with ($\alpha$-$^{32}$P)ATP using terminal transferase. This enzyme adds ($^{32}$P)AMP to the 3' end of the oligo. A commercial 3' end labeling kit (Perkin Elmer) is used to perform the reaction. The extra adenosine group is not expected to interfere with binding of the labeled oligo to the immobilized avidin monolayer. Radiolabeling efficiency is determined using a similar procedure as described before with equation (1). The specific activity is determined using a UV-vis spectrophotometer at 260 nm. After self-assembly of the radiolabeled anti-T3 onto the avidin monolayer, the probe surface concentration is determined according to equation (2) using the radioisotope detector. The surface concentration of the respective nanostructure is compared to that obtained for a reference sample. The derivatization procedure for the nanocavities may need to be adjusted as a result of this comparison, either by adjusting concentration of anti-T3 in solution or by adjusting the adsorption time.

4.3 Comparison of Fluorescence Enhancement

Detailed, comparative studies of the total fluorescence enhancement by each of the three architectures are performed. Measurements by Lakowicz' group (J. Malicka, I. Gryczynski, Z. Gryczynski, and J. R. Lakowicz, "Effects of fluorophore-to-silver distance on the emission of cyanine-dye-labeled oligonucleotides," Analytical Biochemistry 315, 57-66 (2003)) showed that the fluorescence lifetime of Cy-5 can be reduced from about 1.3 ns to less than 100 ps on nanostructured metallic surfaces, which is one reason why it is necessary to build a system with such small time resolution. In a simplified phenomenological model, the total fluorescence enhancement for all three architectures is given by the product of three factors—$M_{tot}=M_{SP}M_{rad}M_{rate}$, where $M_{SP}$ is the enhancement factor of the incident intensity due to surface plasmon coupling, $M_{rad}$ is the enhancement in fluorescence due to interaction of the molecular radiative dipole with the metallic nanostructure (L. A. Blanco and F. J. G. do Abajo, "Spontaneous light emission in complex nanostructures," Physical Review B 69, 205414 (2004); Y. Liu and and S. Blair, "Enhanced fluorescence transduction properties of metallic nanocavity arrays," submitted to IEEE Journal of Selected Topics in Quantum Electronics (2005)), and $M_{rate}$ is the enhancement factor associated with increase in the radiative transition rate (J. Malicka, I. Gryczynski, Z. Gryczynski, and J. R. Lakowicz, "Effects of fluorophore-to-silver distance on the emission of cyanine-dye-labeled oligonucleotides," Analytical Biochemistry 315, 57-66 (2003); L. A. Blanco and F. J. G. do Abajo, "Spontaneous light emission in complex nano-structures," Physical Review B 69, 205414 (2004)). The product $M_{yield}=M_{rad}M_{rate}$ results in an apparent increase in fluorescence yield, even though the actual quantum efficiency may not be greatly increased. The fluorescence quantum efficiency of a fluor is given by $QE=k_r/(k_r+k_{nr})$ where $k_r$ is the radiative rate and $k_{nr}$ is the nonradiative rate of de-excitation. In the case where the radiative rate is modified to a new value $k'_r$, the fluorescence enhancement is given by the factor $M_{rate}=QE'/QE$, where $QE'=k'_r/(k'_r+k_{nr})$. The amount of enhancement therefore depends strongly on the native QE of the fluor. For Cy-5, QE~28%; therefore, QE can be increased by a maximum of 3.6 times. However, proximity of a fluor to a metal surface can introduce new non-radiative pathways, such as energy transfer to phonons or surface electromagnetic waves. This can also result in a reduction in fluorescence lifetime with comparable reduction in Q, leaving yield unchanged.

Three types of measurements are performed to determine these factors and to compare the three architectures. Measurements of total fluorescence output and photobleaching times are performed as compared to reference surfaces. These measurements allow for estimates of $M_{SP}$ and $M_{yield}$. Fluorescence lifetime measurements are performed, from which the relative contributions of $M_{rad}$ and $M_{rate}$ can be estimated. Initial measurements are performed using Cy-5 labeled avidin, for which the fluor-to-metal separation is about 5 nm. Because the three enhancement factors may have strong dependence on this separation (as shown in related work for Cy-5 on nanostructured silver surfaces, for which the maximum enhancement occurred at 9 nm separation (J. Malicka, I. Gryczynski, Z. Gryczynski, and J. R. Lakowicz, "Effects of fluorophore-to-silver distance on the emission of cyanine-dye-labeled oligonucleotides," Analytical Biochemistry 315, 57-66 (2003))), a simple technique is employed to experimentally study this distance dependence using alternating layers of avidin and biotinylated BSA (BBSA). The monolayer sequence starts with avidin:Cy-5; the next step in the sequence is avidin:BBSA:avidin:Cy-5; and so on. At each step, layer thickness is measured by ellipsometry and surface concentration measured by radiolabeling.

For each architecture, a rigorous electromagnetic simulation (using FEMLAB) of the radiative properties of a dipole (using all orientations) is performed, either within a metallic nanocavity or adjacent to a metallic nanoparticle. In order to mimic experimental conditions, the dipole-metal distance is varied from about 5 nm to about 25 nm. Combined with the experimental results, the results of these simulations can provide further insight into the photophysical processes occurring as the result of proximity to the metallic nanostructures. These studies also determine the maximum oligo lengths that can be employed while retaining the benefits of enhanced fluorescence; preliminary studies suggest that 60-base oligo's still maintain significant enhancement (Y. Liu and S. Blair, "Enhanced fluorescence transduction properties of metallic nanocavity arrays," submitted to IEEE Journal of Selected Topics in Quantum Electronics (2005)) (i.e., greater than half the maximum) within a nanocavity.

Nanocavity array architecture. Previous studies indicate that the intensity enhancement factor due to surface plasmon coupling $M_{SP}$ is about a factor of 2, but with the new symmetric structure described herein, this factor may increase to nearly 7 (H. J. Lezec and T. Thio, "Diffracted evanescent wave model for enhanced and suppressed optical transmission through subwavelength hole arrays," Optics Express 12, 3629-3651 (2004)). The origin of the excitation enhancement within the nanocavities results from the fact that under the condition of enhanced transmission (Y. Liu and S. Blair, "Fluorescence enhancement from an array of sub-wavelength metal apertures," Optics Letters 28, 507-509 (2003)), energy is concentrated within the nanocavities. The periodicity of the nanocavities not only supports coupling incident light from free space into surface plasmon modes, but also modifies the propagation properties of the surface plasmon (I. I. Smolyaninov, W. Atia, and C. C. Davis, "Near-field optical microscopy of two-dimensional photonic and plasmonic crystals," Physical Review B 59, 2454-2460 (1999)) through coherent scattering off the walls of the nanocavities, which results in constructive interference within the nanocavities. Previous studies using random nanocavity arrangements also indicated that the net enhancement of fluorescence yield ranged from about 9 for 150 nm diameter cavities to about 7 for 200 nm diameter cavities. This observation suggests a strong influence of the nanocavity geometry on the emission properties of the fluors, most likely based upon the nanocavity aspect ratio h/d, where h is the height. This effect can be studied experimentally by using nanocavity diameters ranging from 100-250 nm in diameter and comparing with results from simulation. As a result of the geometric dependence, the experimental finding may differ from that of Lakowicz (J. Malicka, I. Gryczynski, Z. Gryczynski, and J. R. Lakowicz, "Effects of fluorophore-to-silver distance on the emission of cyanine-dye-labeled oligonucleotides," Analytical Biochemistry 315, 57-66 (2003)), for example, where the enhancement effects occurred at a nanostructured planar surface, which is known to result in an increase in radiative rate (A. Wokaun, H.-P. Lutz, A. P. King, U. P. Wild, and R. R. Ernst, "Energy transfer in surface enhanced luminescence," Journal of Chemical Physics 79, 509-514 (1983)).

In these measurements, fluorescence output from periodic and random nanocavity arrays are compared to the output from a reference surface that consists of a quartz surface with the same surface concentration (as determined by radiolabeling). The output from the nanocavity arrays is normalized to the fill-fraction of the fluors, given by $\eta_f=\pi dh/\Lambda^2$ (which is different than the nanocavity fill fraction $\eta=\pi(d/2)^2/\Lambda^2$) since the fluors cover only the inner walls of the nanocavities. The total fluorescence enhancement factor $M_{tot}$ is given by the ratio of normalized fluorescence output from the periodic array to the reference surface, while the surface plasmon excitation enhancement factor $M_{SP}$ is given by the ratio of fluorescence between the periodic and random array. From these quantities, an apparent increase in fluorescence yield can be determined by the ratio $M_{yield}=M_{tot}/M_{SP}$, but further measurements can be compared to compare photobleaching times and fluorescence lifetimes across the periodic and random nanocavity array geometries and the reference in order to obtain a better understanding of the influence of the nanocavity geometry on the photophysical processes.

All measurements using three different samples are performed for each geometry. Multiple samples can be fabricated on each substrate to greatly improve the efficiency. The standard deviations from these measurements reflect variations in pattern fabrication, monolayer coating, and optical alignment and detection. With our previous methods, we achieved a standard deviation of less than 10% of the mean. The new fabrication methods and surface modification procedures are expected to reduce the deviation to less than 5%.

Bullseye nanocavity architecture. The main reason why the surface plasmon enhancement factor for the nanocavity arrays is small is due to the fact that the periodicity of the nanocavities themselves is used to couple incident light into surface plasmon modes. The fill fraction of the nanocavities is small (resulting in a weak diffraction grating) in order to keep $\Lambda > \lambda$ and to improve background isolation. The bullseye nanocavity geometry breaks these constraints by using a separate, more efficient, structure for grating coupling into surface plasmon modes—corrugated annular rings—which redistributes a much larger fraction of incident light into the nanocavity in the center. Measurements of second-harmonic generation through the bullseye nanocavity compared to a single, bare nanocavity (A. Nahata, R. A. Linke, T. Ishi, and K. Ohashi, "Enhanced nonlinear optical conversion using periodically nanostructured metal films," Optics Letters 28, 423-425 (2003)) indicate that the surface plasmon intensity enhancement within the bullseye nanocavity $M_{SP}\sim 100$. The main disadvantage of the bullseye architecture is that the annular ring structure is significantly larger than the nanocavity, reducing the density of detection sites within a zone.

As before with the nanocavity array architecture, measurements across three samples—a 3×3 bullseye array, and 3×3 nanocavity array with $\Lambda=S=25$ µm, and the quartz surface, are compared. The purpose of the 3×3 nanocavity array is to maintain the same fluor fill fraction $\eta_f=\pi dh/S^2$ while isolating surface plasmon excitation enhancement from nanocavity related effects. At 25 µm spacing, which is greater than the surface plasmon attenuation length, these nanocavities do not coherently interact and therefore act as independent cavities. From these measurements, significantly larger excitation enhancement factors $M_{SP}$ is expected with very similar yield enhancements $M_{yield}$. Because of the annular corrugation surrounding each nanocavity in the bullseye structure, the radiative properties of the fluor could be modified from that of the bare nanocavity, which would affect the radiative efficiency $M_{rad}$. This can be verified with electromagnetic simulation. Even with the possible modification of $M_{rad}$, it is anticipated that it is not necessary to repeat the exhaustive studies comparing enhancement effects versus nanocavity diameter d and fluor-to-sidewall separation, thus requiring far fewer bullseye patterns be fabricated.

Nanoparticle architecture. Large surface enhancement effects by metallic nanoparticles have been known for over 20 years (M. Fleischmann, P. J. Hendra, and A. J. McQuillan, "Raman spectra of pyridine adsorbed at a silver electrode," Chemical Physics Letters 26, 163-166 (1974); H. G. Craighead and A. M. Glass "Optical absorption of small metal particles with adsorbed dye coats," Optics Letters 6, 248-250 (1981)) owing to the large absorption cross-section associated with the local plasmon resonance of the nanoparticle. The wavelength of the peak absorption due to the local plasmon resonance is determined by the geometry of the nanoparticle. The nanoparticles are elliptical in shape with major axis about 110 nm, minor axis about 100 nm, and thickness about 30 nm, which places the peak of the local plasmon absorption near 633 nm in one linear polarization state (the state of polarization of the excitation light) and a peak in the local plasmon resonance near 670 nm (the peak fluorescence wavelength for Cy-5) for the orthogonal state of polarization. The use of an elliptical nanoparticle can produce a double resonance effect (H. Ditlbacher, N. Felidj, J. R. Krenn, B. Lambprecht, A. Leitner, and F. R. Aussenegg, "Electromagnetic intereaction of fluorophores with designed 2D silver nanoparticle arrays," Applied Physics B 73, 373 (2001)) to maximize fluorescence output. With the nanoparticle array, since the nanoparticles are non-interacting, there is no way to directly isolate the excitation enhancement factor $M_{SP}$ from $M_{yield}$; therefore, the comparisons are based upon the quartz reference surface. The measured fluorescence from the nanoparticle array is normalized to the fill fraction of the nanoparticles $\eta=\pi(d/2)^2/\Lambda^2$ and compared to the reference sample to obtain the total fluorescence enhancement factor. This fill fraction is significantly greater than for the nanocavity array as $\Lambda$ is much shorter.

For the nanoparticle array, $M_{SP}$ can be estimated from the ratios of photobleaching times and fluorescence lifetimes between the nanoparticle array and reference surface. As with the nanocavity array, these measurements are performed as a function of fluor-particle spacing, but expect to obtain results qualitatively similar to Lakowicz (J. Malicka, I. Gryczynski, Z. Gryczynski, and J. R. Lakowicz, "Effects of fluorophore-to-silver distance on the emission of cyanine-dye-labeled oligonucleotides," Analytical Biochemistry 315, 57-66 (2003)). Overall, total enhancement factors $M_{tot} > 10$ is anticipated (H. Ditlbacher, N. Felidj, J. R. Krenn, B. Lambprecht, A. Leitner, and F. R. Aussenegg, "Electromagnetic intereaction of fluorophores with designed 2D silver nanoparticle arrays," Applied Physics B 73, 373 (2001); J. Malicka, I. Gryczynski, and J. R. Lakowicz, "DNA hybridization assays using metal-enhanced fluorescence," Biochemical and Biophysical Research Communications 306, 213-218 (2003); J. Malicka, I. Gryczynski, Z. Gryczynski, and J. R. Lakowicz "Effects of fluorophore-to-silver distance on the emission of cyanine-dye-labeled oligonucleotides," Analytical Biochemistry 315, 57-66 (2003)), with the majority of the enhancement due to $M_{SP}$. The total fluorescence enhancement is anticipated to be more sensitive to separation for the nanoparticles than for the nanocavity architectures.

The surface plasmon enhancement factor $M_{SP}$ represents an additional enhancement over the yield enhancement given by $M_{yield}=M_{rad}M_{rate}$. This additional factor is important in situations where fluorescence transduction is not photobleaching limited. One situation is in the use of quantum dot fluorescence labels (M. B. Jr., M. Moronne, P. Gin, S. Weiss, and A. P. Alivisatos, "Semiconductor nanocrystals as fluorescent biological labels," Science 281, 2013-2016 (1998); W. C. W. Chan and S. Nie "Quantum dot bioconjugates for ultrasensitive nonisotropic detection," Science 281, 2016-2018 (1998).), which do not significantly photobleach. With metallic nanostructure arrays comprising a single zone, we obtain the practical advantages of an additional fluorescence signal increase by the factor $M_{SP}M_{yield}$ for the same number of fluorescing molecules, or a reduction in the number of molecules by the factor $M_{SP}M_{yield}$ with the same fluorescence level, as compared to direct excitation on a quartz substrate with the same zone area. The other situation is that of simultaneous transduction of multi-zone sensing arrays, in which the incidence light is divided equally among all zones. The practical advantage, then, even in the case of fluors that photobleach, is that spreading the light across MSP zones will result in $M_{yield}$ times more output from each zone with the same bleaching time, as compared to a single zone on a quartz substrate with the same number of molecules per zone. One could also excite $M_{SP}M_{yield}$ zones with the same fluorescence output from each zone as the quartz substrate, but with a much longer time to photobleach. These factors do not take into account the other significant advantage of the nanostructure array architectures, that of background isolation, which further improves these scalings by at least another order of magnitude.

4.4 Comparison of Sensitivity in Real-Time Hybridization

The performance advantages of the nanostructure architectures are quantified through the study of real-time hybridization kinetics on a single zone using fluorescence transduction in the presence of varying concentrations of background species. Instead of using RNA as the target species (as would be the case in direct expression analysis), end-labeled single-stranded DNA (i.e., an oligonucleotide of 20-base length) is used. The reason for this is that DNA is significantly more robust and requires fewer precautions in sample handling and storage, therefore simplifying experimental procedures. These results are highly relevant to the direct analysis of expressed RNA, which can also be performed using the structures as described herein. The T3 polymerase promotor site is used as a model system; T3 and complementary anti-T3 are commercially available, and can be fluorescently labeled with Cy-5. Capture oligonucleotides (anti-T3 for these studies) are selectively immobilized as described previously. Sample solution containing fluorescently labeled target and non-target species are introduced to the surface using a flow cell (see FIG. 4), which resides on the top surface of the nanostructure samples. A kinetic curve is analyzed using the two-compartment model as described previously. These parameters are illustrated in FIG. 6. The purpose for using the two-compartment model is that, through the fitting constant $k_M$, the effect of mass transport to the sparse array of detection sites can be determined and compared to a planar waveguide sensing modality in which the fill fraction is 100%. In order to differentiate the effects of non-specific binding, the two-compartment model is modified to describe the binding of two species to the surface with association constants $k_{a1}$ and $k_{a2}$. In this case, two bound concentrations B1(t) and B2(t) are obtained, and the density of available binding sites are given by RT−B1(t)−B2(t). The effects of dissociation for the non-specific species may also be incorporated. It is not be noted that the ultimate goal for expression arrays is to use the two-compartment model to analyze the kinetic curve at each hybridization zone to obtain the unknown concentration $C_T$ of the desired target in solution.

Before the real-time hybridization experiments are performed, a calibration between bound surface concentration and fluorescence intensity is performed. Using radiolabeling as described previously, the bound probe concentration can be obtained. The same surface modification procedures with Cy-5 end-labeled anti-T3 (with labeling ratio determined by UV-vis absorption) can be performed to allow direct relation between measured fluorescence intensity and bound concentration. This relationship can then be used in conjunction with the two-compartment model to determine the detection limits in terms of the number of bound target molecules.

Determination of detection sensitivity—nanocavity architectures. In this section, fluorescence isolation from unbound species is verified, and the detection sensitivity is determined taking into account non-specific binding for the periodic nanocavity array and 3×3 bullseye array. Because detectable fluorescence can only be produced from within a nanocavity, random variation in fluorescence from non-target molecules only occurs when those molecules randomly diffuse into and out of the nanocavity (although some fraction may non-specifically bind). The nanocavity surface area represents a fraction $\eta$ of the total zone area ($\eta \sim$1-4% for the nanocavity arrays and $\eta \sim$0.01% for the bullseye arrays), so that the background signal from unbound species should be less by a factor of approximately $1/\eta$ than in other washless, surface selective fluorescence sensors such as a planar waveguide or fluorescence-SPR where the sensing surface represents 100% of the zone area.

Because the transduction area in the nanocavity architectures is so small, diffusion of the target molecules into the sensing regions may be slower than if the transduction area were 100% of the sensing area. The first step is to study hybridization kinetics of the labeled target as a function of target concentration in solution, as compared to a planar waveguide. Target oligos (T3), labeled at the 5' end with Cy-5 dye are prepared in solution with a concentration $C_n$, where n is the trial number. Typical Molar concentrations range from $10^{-8}$ to $10^{-12}$. When introduced into the flow cell, T3 specifically binds to probe oligos on the capture monolayer and form hybridized DNA. The hybridization kinetic curve 74 is measured for each $C_n$ through the time dependence of the fluorescence excited by light intensity within each nanocavity (as in FIG. 5). Both association 76 (i.e., binding) and dissociation 78 curves are obtained, as illustrated in FIG. 7. The dissociation curve 78 are generated by flowing buffer solution through the flow cell, and allows determination of $k_d$ (which will essentially be zero for specific binding, but non-zero for non-specific binding, as described in the next paragraph). By comparing the kinetic curves between the two nanocavity architectures and the waveguide, with greatly different fill fractions, the increase in diffusion time can be determined via the parameter $k_M$.

The next step is to perform the same measurements using a second labeled sequence of the same length as T3/anti-T3 to determine the kinetic coefficients in the two-compartment model for non-specific binding. The sequence of these "background" oligos is chosen so as not to specifically bind to either the target or probe molecules. These background oligos diffuse into the nanocavities and produce a random background signal, which could mask the kinetic curve produced by bound species, and may also non-specifically bind, which produces a signal that mimicks the kinetics of the target species (but with a different rate and equilibrium value (H. Dai, M. Meyer, S. Stepaniants, M. Ziman, and R. Stooughton, "Use of hybridization kinetics for differentiating specific from non-specific binding to oligonucleotide microarrays," Nucleic Acids Research 30, (2002))). As before, these measurements are made as a function of $C_n$, where larger concentrations in the range $10^{-6}$ to $10^{-10}$ are used. From the determination of the kinetic coefficients ($k_{a2}$ and $k_{d2}$, which should be relatively constant across concentration of non-specific species), the modified dual-rate two-compartment model can then be used to differentiate between specific and non-specific binding, where the fitting parameters in the model are $C_1$ and $C_2$.

Three sets of measurements are made to determine the detection sensitivity. The first set is as a function of target concentration $C_n$, where the concentration of non-specific oligos is also $C_n$. This situation simulates the conditions for a two-zone sensor array. The second set has target concentration $C_n$, but non-specific concentration $10 C_n$, thus simulating a 10-zone array. The final set has a non-specific concentration of $100 C_n$. From the two-compartment model, the minimum detectable target concentration and the associated number of bound target molecules can be determined. It is anticipated that the detection limit will be a factor of $M_{tot}/\eta$ lower for the nanocavity architectures than the waveguide (taking into account the normalization between surface intensity of the evanescent field of the waveguide and the intensity of direct excitation on the quartz reference surface from which $M_{tot}$ was derived, where this normalization factor will be of order 1).

Determination of detection sensitivity—nanoparticle architecture. Estimation of the expected signal to background ratio in the nanoparticle architecture is more involved as fluorescence contribution from non-target species can occur either near the nanoparticle surface or between the nanoparticles. The excitation geometry that minimizes contribution from species residing between nanoparticles is shown in FIG. 1, in which the local plasmon resonance of the nanoparticles is excited via the evanescent wave of a prism. These mean that only unbound species that randomly diffuse to within about 100 nm of the surface produce a contribution. The signal to background ratio of the nanoparticle arrays is given by $M_{tot}/(\eta M_{tot}+(1-\eta))$; therefore, for very large total fluorescence enhancement factors $M_{tot}>>(1-\eta)/\eta$, the background isolation scales the same as the nanocavity architectures. The same experimental procedures used for the nanocavity architectures are repeated for the nanoparticle architecture.

The detection sensitivities are critically compared across the three architectures. As discussed previously, the nanocavity architectures are expected to have the greatest background isolation, with the bullseye having the greatest signal to background ratio due to its large surface plasmon enhancement and very low fill fraction. These bullseye structures are the most promising architecture for the implementation of very high sensitivity detection that can operate with unbiased real populations, as the large surface plasmon intensity enhancement allows efficient scaling to large arrays, where each zone retains the benefit of yield enhancement given by $M_{yield} \sim 10$.

Two additional sets of studies can also be performed: 1) single base-pair mismatch discrimination, which is performed in the same manner as the non-specific binding studies, except that the temperature of the nanostructure array is elevated to near the heteroduplex melting temperature, and 2) binding studies using target and non-target species of 60-base length (where the bottom 20 bases of the target are complementary to anti-T3) in order to provide additional relevant results to situations encountered in expression analysis.

Although the description included herewith contains many specifics, these should not be construed as limiting the scope of the invention, but merely as providing illustrations of some of the presently preferred embodiments. Similarly, other embodiments of the invention may be devised which do not depart from the spirit or scope of the invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

What is claimed is:

1. A detection-enhancement element for a biological assay, comprising:
    a substrate;
    a metallic layer on at least one surface of the substrate and including at least one nanocavity; and
    capture molecules within the at least one nanocavity;
    wherein a surface of the metallic layer is passivated to prevent specific and non-specific binding of the capture molecules to the metallic layer outside of the at least one nanocavity.

2. The detection-enhancement element of claim 1, wherein the metallic layer comprises gold.

3. The detection-enhancement element of claim 1, wherein the at least one nanocavity enhances a signal representative of an amount of at least one analyte present in a sample.

4. The detection-enhancement element of claim 3, wherein the metallic layer used with the substrate enhances a fluorescence signal that indicates binding of at least one of an analyte and a competing molecule with a capture molecule within the at least one nanocavity.

5. The detection-enhancement element of claim 3, wherein the nanocavity enhances the signal by a factor at about 2 or more.

6. The detection-enhancement element of claim 3, wherein the nanocavity enhances the signal by a factor of about 3 or more.

7. The detection-enhancement element of claim 3, wherein the nanocavity enhances the signal by a factor at about 6 or more.

8. The detection-enhancement element of claim 3, wherein the nanocavity enhances the signal by a factor at about 12 or more.

9. The detection-enhancement element of claim 1, wherein the at least one nanocavity has a width of about 100 nm to about 150 nm.

10. The detection-enhancement element of claim 9, wherein the width is a diameter.

11. The detection-enhancement element of claim 1, wherein the at least one nanocavity is spaced, on average, about 0.5 micrometers to about 0.6 micrometers apart from another nanocavity.

12. The detection-enhancement element of claim 1, comprising a plurality of nanocavities organized in an array.

13. The detection-enhancement element of claim 1, comprising a plurality of nanocavities distributed randomly over the substrate.

14. The detection-enhancement element of claim 1, wherein the at least one nanocavity is surrounded by a predetermined corrugated pattern of increased surface area features.

15. The detection-enhancement element of claim 1, wherein the passivated layer comprises polyethylene glycol (PEG)-thiol.

16. The detection-enhancement element of claim 1, wherein the at least one nanocavity comprises a polygonal shape having a diameter, wherein the diameter comprises the largest distance between any pair of vertices of the polygonal shape.

17. An apparatus for use in a biomolecular assay, comprising:
- a substrate;
- a metallic layer on at least one surface of the substrate, the metallic layer including a plurality of nano cavities;
- wherein the nanocavities create an exposed surface of the substrate and the exposed surface of the substrate is passivated; and
- capture molecules within the plurality of nanocavities on a surface that has not been passivated.

18. The apparatus of claim 17, wherein at least some of the capture molecules are immobilized to surfaces of the metallic layer within the plurality of nanocavities.

19. The apparatus of claim 17, wherein nanocavities of the plurality of nanocavities enhance a signal representative of an amount of at least one analyte present in a sample.

20. The apparatus of claim 19, wherein the metallic layer enhance a fluorescence signal that indicates binding of at least one of an analyte and a competing molecule with a capture molecule within a nanocavity of the metallic substrate.

21. The apparatus of claim 17, wherein the substrate comprises quartz.

22. The apparatus of claim 17, wherein the metallic layer comprises gold.

23. The apparatus of claim 17, wherein nanocavities of the plurality are surrounded by a predetermined corrugated pattern of increased surface area features.

24. The apparatus of claim 17, wherein the passivated layer comprises polyethylene glycol (PEG)-thiol.

25. A detection-enhancement element for a biological assay, comprising:
- a substrate;
- a metallic layer on at least one surface of the substrate and including at least one nanocavity;
- wherein the at least one nanocavity creates an exposed surface of the substrate and the exposed surface of the substrate is passivated; and
- capture molecules within the at least one nanocavity immobilized to a surface of the metallic layer that has not been passivated.

26. A detection-enhancement element for a biological assay, comprising:
- a substrate;
- a metallic layer on at least one surface of the substrate and including at least one nanocavity, wherein the at least one nanocavity creates an exposed surface of the substrate and the exposed surface of the substrate is passivated;
- a coating film passivating a substantial portion of the metallic layer; and
- capture molecules immobilized to a sidewall within the at least one nanocavity that has not been passivated.

27. A detection-enhancement element for a biological assay, comprising:
- a substrate;
- a metallic layer on at least one surface of the substrate and including at least one nanocavity surrounded by a predetermined corrugated pattern of increased surface area features; and
- capture molecules within the at least one nanocavity.

* * * * *